(12) United States Patent
Maeda et al.

(10) Patent No.: US 9,155,847 B2
(45) Date of Patent: Oct. 13, 2015

(54) NEBULIZERS AND FUNCTION UNITS ATTACHABLE TO NEBULIZER

(75) Inventors: Masao Maeda, Kyoto (JP); Kei Asai, Otsu (JP); Kentaro Mori, Nara (JP); Makoto Tabata, Kyoto (JP); Masayuki Esaki, Ibaraki (JP); Toshiro Furusawa, Kyotanabe (JP); Yusaku Sakoda, Shiojiri (JP); Yusuke Kato, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 1098 days.

(21) Appl. No.: 13/207,881

(22) Filed: Aug. 11, 2011

(65) Prior Publication Data
US 2011/0290241 A1 Dec. 1, 2011

Related U.S. Application Data

(63) Continuation of application No. PCT/JP2010/051088, filed on Jan. 28, 2010.

(30) Foreign Application Priority Data

Mar. 17, 2009 (JP) ................ 2009-064615

(51) Int. Cl.
| | |
|---|---|
| *A61M 11/00* | (2006.01) |
| *A61M 15/00* | (2006.01) |
| *A61M 16/00* | (2006.01) |

(52) U.S. Cl.
CPC .......... *A61M 11/005* (2013.01); *A61M 15/0015* (2014.02); *A61M 2016/0024* (2013.01); *A61M 2016/0027* (2013.01); *A61M 2205/50* (2013.01)

(58) Field of Classification Search
CPC .......... A61M 15/0085; A61M 15/009; A61M 15/06; A61M 11/005; A61M 15/0015; A61M 2016/024; A61M 2016/027; A61M 2205/50

USPC ......... 128/200.14, 200.16; 131/273; 239/338, 239/370
See application file for complete search history.

(56) References Cited

U.S. PATENT DOCUMENTS

| | | | |
|---|---|---|---|
| 4,677,975 A | 7/1987 | Edgar et al. | |
| 5,511,539 A * | 4/1996 | Lien .................. | 128/200.21 |

(Continued)

FOREIGN PATENT DOCUMENTS

| | | |
|---|---|---|
| CN | 2905088 Y | 5/2007 |
| CN | 201067728 Y | 6/2008 |

(Continued)

OTHER PUBLICATIONS

Chinese Office Action issued in Application No. 201080012397.6; Dated Jul. 23, 2013 (With Translation).

(Continued)

*Primary Examiner* — Justine Yu
*Assistant Examiner* — Timothy Stanis
(74) *Attorney, Agent, or Firm* — Oliff PLC

(57) ABSTRACT

A nebulizer includes a main body unit, an atomization unit, and a breath detection unit, which is a function unit for realizing an additional function of the nebulizer. The main body unit and the atomization unit are separable. The atomization unit includes a storage section for storing the medicinal solution, and an atomizing section for spraying the medicinal solution by atomizing the medicinal solution in the storage section. The main body unit includes a control circuit for performing control to operate the atomizing section. The breath detection unit is attachable between the main body unit and the atomization unit.

11 Claims, 19 Drawing Sheets

(56) References Cited

U.S. PATENT DOCUMENTS

Figure 1:
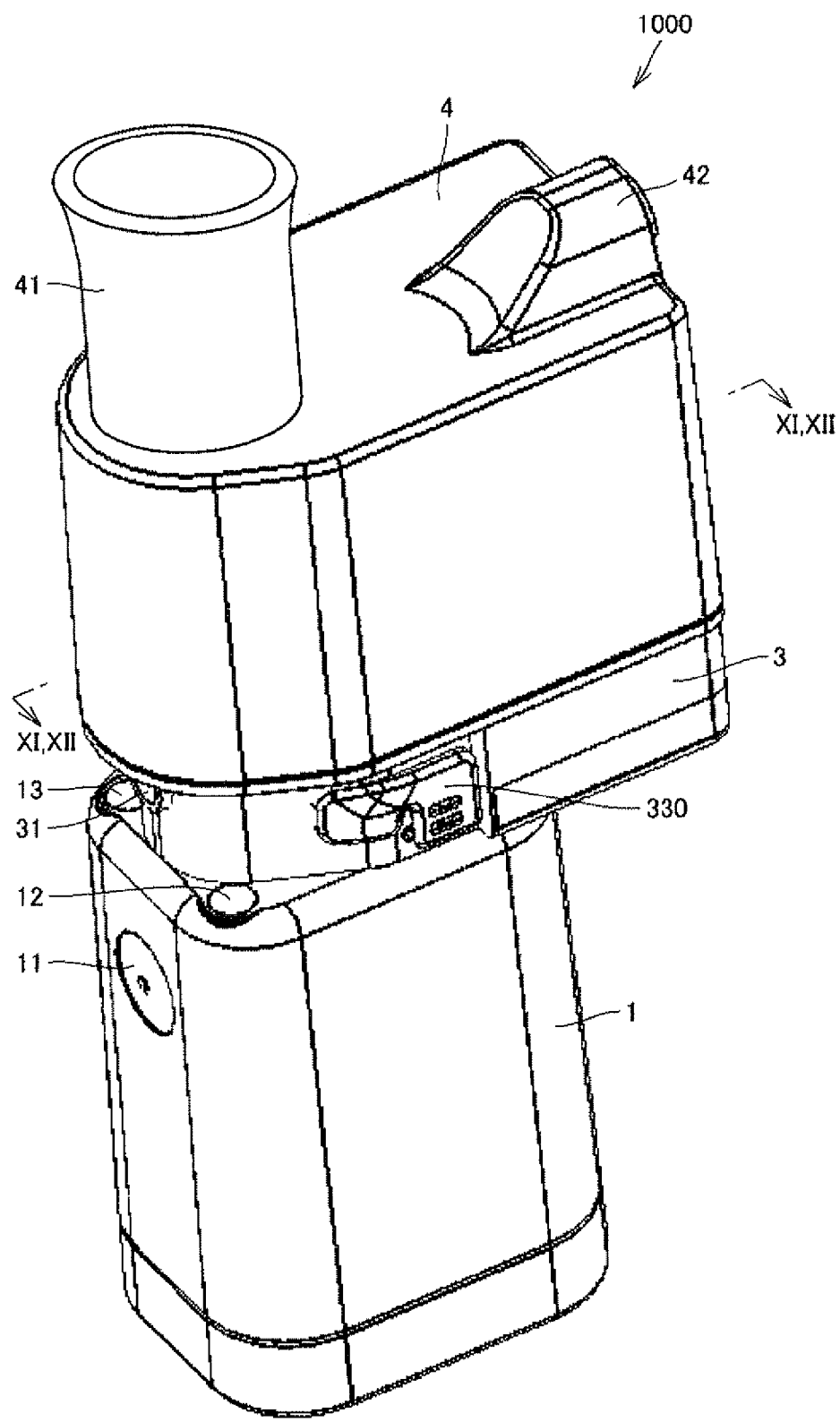

| | | | |
|---|---|---|---|
| 5,921,232 A * | 7/1999 | Yokoi et al. | 128/200.14 |
| 6,029,659 A * | 2/2000 | O'Connor | 128/203.12 |
| 6,116,233 A | 9/2000 | Denyer et al. | |
| 7,347,200 B2 * | 3/2008 | Jones et al. | 128/200.23 |
| 7,673,812 B2 * | 3/2010 | Weng et al. | 239/102.2 |
| 2003/0062038 A1 | 4/2003 | Tanaka et al. | |
| 2005/0016550 A1* | 1/2005 | Katase | 131/194 |
| 2006/0201500 A1* | 9/2006 | Von Hollen et al. | 128/203.12 |
| 2006/0243274 A1* | 11/2006 | Lieberman et al. | 128/200.14 |

FOREIGN PATENT DOCUMENTS

| | | |
|---|---|---|
| JP | A-61-179158 | 8/1986 |
| JP | A-06-190044 | 7/1994 |
| JP | A-2002-336281 | 11/2002 |
| JP | A-2003-102837 | 4/2003 |
| JP | A-2005-102899 | 4/2005 |
| JP | A-2005-278742 | 10/2005 |
| WO | WO 2006/128567 A1 | 12/2006 |

OTHER PUBLICATIONS

Feb. 13, 2014 Office Action issued in Chinese Patent Application No. 201080012397.6 (with English translation).

International Search Report issued in Application No. PCT/JP2010/051088; Dated Feb. 23, 2010 (With Translation).

* cited by examiner

NEBULIZERS AND FUNCTION UNITS ATTACHABLE TO NEBULIZER

TECHNICAL FIELD

The present invention relates to nebulizers and function units attachable to the nebulizer, and in particular, to a nebulizer in which a main body unit and an atomization unit are separable, and a function unit attachable to the nebulizer.

BACKGROUND ART

A nebulizer in which a main body unit and an atomization unit are separable is commercially available from the related art (e.g., mesh type nebulizer NE-U22 manufactured and sold by applicant). Since the atomization unit including a medicinal solution tank or the like can be separated from the main body unit, the atomization unit to which the medicinal solution easily attaches can be easily cleaned.

The nebulizer configured by the main body unit and the atomization unit realizes the basic function of the nebulizer of atomizing the medicinal solution.

A nebulizer mounted with an additional function of changing the spray state in addition to the basic function also exists. For example, a nebulizer having a breath detection function of detecting the breathing state (exhale, inhale) of the patient and capable of spraying only at the time of inhaling also exists. For example, WO 2006/128567 pamphlet (patent document 1) discloses detecting of breathing by a structure of opening and closing a spray gas opening from an inner pressure of an inhaler by breathing. Japanese Unexamined Patent Publication No. 6-190044 (patent document 2) discloses detecting of breathing by sound.

In the field of medical apparatuses, a function module type medical care device has been proposed from the related art as shown in Japanese Unexamined Patent Publication No. 2002-336281 (patent document 3). Such medical care device includes a common function section including at least one of a display unit, an operation unit, and a power supply unit, and a module connecting section for connecting a function module having an individual medical care function in a changeable manner, where the medical care function of the connected function module is used in the common function section.

PRIOR ART DOCUMENTS

Patent Documents

Patent Document 1: WO 2006/128567 pamphlet
Patent Document 2: Japanese Unexamined Patent Publication No. 6-190044
Patent Document 3: Japanese Unexamined Patent Publication No. 2002-336281.

SUMMARY OF THE INVENTION

Problems to be Solved by the Invention

In the conventional nebulizer described above, the mounted function is fixed. Thus, the nebulizer mounted with the necessary function needs to be prepared for each user (patient).

However, if the user already has a nebulizer, the addition of other functions may be desired in addition to the function mounted on the nebulizer, or the deletion of the mounted function may be desired. In such a case, the change of functions required by the patient cannot be responded with the conventional nebulizer.

In the technical field other than the nebulizer, a medical care device (dental device) in which a function module having individual medical care function can be exchanged has been proposed, as in Japanese Unexamined Patent Publication No. 2002-336281 (patent document 3). However, a nebulizer in which the additional function specific to the nebulizer, that is, function for changing to a specification of high treatment effect and/or optimizing according to the status of the user can be added or deleted has not been proposed at all.

In light of the foregoing problems, it is an object of the present invention to provide a nebulizer in which a function (additional function) for changing to a specification of high treatment effect and/or optimizing according to the status of the user can be easily added or deleted by the user himself/herself.

Means for Solving the Problem

In accordance with one aspect of the present invention, a nebulizer is a nebulizer for spraying medicinal solution, the nebulizer including first and second units; wherein the first and second units are separable; the first unit includes a storage section for storing the medicinal solution, and an atomizing section for spraying the medicinal solution by atomizing the medicinal solution in the storage section; the second unit includes a controller for performing control to operate the atomizing section; a third unit for realizing an additional function of the nebulizer is further arranged; and the third unit is attachable between the first unit and the second unit.

The third unit preferably includes a relay portion for electrically connecting the controller and the atomizing section.

The third unit preferably realizes a function of changing a spray state by the atomizing section as the additional function.

The third unit preferably includes a detection unit for detecting a breathing state of the user; and an atomization control unit for causing the atomizing section to atomize the medicinal solution only in inhaling according to the detection result by the detection unit.

The atomizing section preferably includes a vibrator driven to atomize the medicinal solution; the second unit further includes an oscillating section for outputting an oscillation signal for vibrating the vibrator in response to an instruction from the controller; and the atomization control unit receives the oscillation signal output by the oscillating section, and transfers the received oscillation signal to the vibrator only in inhaling.

The third unit preferably includes an adjusting section for adjusting the spray amount per unit time by the atomizing section.

The atomizing section preferably includes a vibrator driven to atomize the medicinal solution; the second unit further includes an oscillating section for outputting an oscillation signal for vibrating the vibrator in response to an instruction from the controller; and the adjusting section adjusts the amplitude or the frequency of the oscillation signal output by the oscillating section, and transfers the adjusted oscillation signal to the vibrator.

The third unit further preferably includes an operating section for receiving an instruction from the user on the spray amount per unit time.

The third unit preferably realizes a function of changing a using method of the nebulizer as the additional function.

In accordance with another aspect of the present invention, a function unit is a function unit, attachable to a nebulizer including first and second units, for realizing an additional function of the nebulizer; wherein the first unit includes a storage section for storing the medicinal solution, and an atomizing section for spraying the medicinal solution by atomizing the medicinal solution in the storage section; the second unit includes a controller for performing control to operate the atomizing section; and a relay portion for electrically connecting the controller and the atomizing section is arranged.

Effect of the Invention

According to the present invention, the function unit for realizing the additional function can be freely attached between the first unit and the second unit. The user himself/ herself can easily add or delete, to and from the existing nebulizer, the function (additional function) for changing to the specification of high treatment effect and/or optimizing according to the status of the user.

BRIEF DESCRIPTION OF THE DRAWINGS

FIG. 1 is a perspective view of an outer appearance of a nebulizer in a usage state according to a first embodiment of the present invention.

FIG. 2 is a perspective view of an outer appearance showing a unit configuration example of the nebulizer according to the first embodiment of the present invention.

FIG. 3 is a view showing a state in which each unit of the nebulizer according to the first embodiment of the present invention is separated.

FIG. 4 is a perspective view of the outer appearance including the upper surface of the main body unit in the first embodiment of the present invention.

FIG. 5 is a bottom view of a breath detection unit in the first embodiment of the present invention.

FIG. 6 is a perspective view of the outer appearance including the upper surface of the breath detection unit in the first embodiment of the present invention.

FIG. 7 is a bottom view of an atomization unit in the first embodiment of the present invention.

FIG. 8 is a block diagram showing one example of a circuit configuration of the nebulizer according to the first embodiment of the present invention.

FIG. 9(A) is a cross-sectional view of the atomization unit shown in FIG. 3 in plane IXA-IXA, FIG. 9(B) is a cross-sectional view of the breath detection unit shown in FIG. 3 in plane IXB-IXB, and FIG. 9(C) is a partial cross-sectional view of the main body unit 1 shown in FIG. 3 in plane IXC-IXC.

FIG. 10 is a cross-sectional view in plane X-X of the breath detection unit shown in FIG. 3.

FIG. 11 is a cross-sectional view describing the operation of the nebulizer at the time of exhaling.

FIG. 12 is a cross-sectional view describing the operation of the nebulizer at the time of inhaling.

FIG. 13 is a view showing an exhaled air valve arranged in the cover unit.

FIG. 14 is a view showing a unit configuration example of a nebulizer of basic specification in each embodiment of the present invention.

FIG. 15 is a block diagram showing one example of a circuit configuration of the nebulizer of basic specification in each embodiment of the present invention.

FIG. 16 is a cross-sectional view describing the electrical connection of the nebulizer of basic specification in each embodiment of the present invention.

FIG. 17 is an outer appearance diagram showing a unit configuration example of a nebulizer according to a second embodiment of the present invention.

FIG. 18 is a block diagram showing one example of a circuit configuration in the second embodiment of the present invention.

FIG. 19 is an outer appearance diagram showing a unit configuration example of a nebulizer according to a third embodiment of the present invention.

EMBODIMENTS FOR CARRYING OUT THE INVENTION

Embodiments of the present invention will be described in detail with reference to the drawings. The same reference numerals are denoted to the same or corresponding portions in the figures, and the description thereof will not be repeated.

First Embodiment (Regarding outline)

First, an outline of a nebulizer 1000 in the present embodiment will be described with reference to FIG. 1 and FIG. 2. The nebulizer 1000 in the present embodiment is assumed as a so-called mesh type.

The nebulizer 1000 includes a main body unit 1, an atomization unit 2, a breath detection unit 3, and a cover unit 4. The main body unit 1 and the atomization unit 2 realize the basic functions of the nebulizer, and the breath detection unit 3 realizes the additional function.

As hereinafter described in detail, the main body unit 1 includes a power supply circuit and a control circuit. A power supply switch 11 for switching ON/OFF of the power of the nebulizer 1000 is arranged on the front surface of the main body unit 1. Two LEDs (Light Emitting Diodes) 12, 13 that emit light of different colors are arranged on the upper surface. The LED 12 outputs a green light, and the LED 13 outputs an orange light. For example, the LED 12 is lighted when the power is turned ON, and the LED 13 is lighted when the battery capacity becomes low (battery low time).

As hereinafter described in detail, the atomization unit 2 includes a medicinal solution storage section for storing medicinal solution, and an atomizing section (mesh and vibrator) for atomizing the medicinal solution. The atomization unit 2 has a spray port 240 for spraying the medicinal solution and an open/close operating portion 241 that can be opened and closed by the user, at the upper part. When the open/close operating portion 241 is opened and closed, the medicinal solution can be easily supplied to the medicinal solution storage section or the medicinal solution storage section can be easily cleaned. The medicinal solution can also be supplied by opening and closing the spray port 240.

The breath detection unit 3 detects the breathing state (exhale, inhale) of the user. The atomization by the atomizing section is executed only in the case of inhaling. In the present embodiment, the breathing state is detected by the pressure sensor. The breath detection unit 3 has, at the upper part, a second tube portion 322 leading to a first tube portion 321 (see FIGS. 9(A) to 9(C) etc.) in a housing 300. An LED 31 is also arranged on the front surface of the breath detection unit 3. The LED 31 is lighted when the capacity of a button type battery 350 (see FIG. 9 etc.), to be described later, in the breath detection unit 3 becomes low (battery low time).

As shown in FIG. 1, the entire atomization unit 2 and one part of the breath detection unit 3 are covered by the cover unit 4 in the usage state. The cover unit 4 is an aiding tool for aiding the detection of breathing and the intake of the medicinal solution, and is integrally formed from a resin material. The cover unit 4 is attached to the breath detection unit 3 by being fitted to a fit-in portion 320 arranged on the side surface of the breath detection unit 3. A packing is interposed between the cover unit 4 and the breath detection unit 3 in a state where the cover unit 4 is attached to the breath detection unit 3. The space inside the cover unit 4 and the outside are thereby maintained in an air tight manner.

A mouth piece (intake port) 41 to be held by the user's mouth can be attached to a tubular portion 420 (see FIG. 11 etc.) at the upper surface of the cover unit 4. The user holds the nebulizer 1000 in the state shown in FIG. 1 by hand, slightly tilts it to the near side, and uses by putting the mouth piece 41 of the cover unit 4 in the mouth. When the user inhales, the atomized medicinal solution sprayed from the spray port 240 of the atomization unit 2 passes through the tubular portion 420 (see FIG. 11 etc.) and the mouth piece 41.

A ventilating portion 42 for ventilating the gas inside and outside the cover unit 4 is further arranged at the upper surface of the cover unit 4. The ventilating portion 42 is formed such that the gas is exhausted to the back side of the nebulizer 1000.

Figure 3:
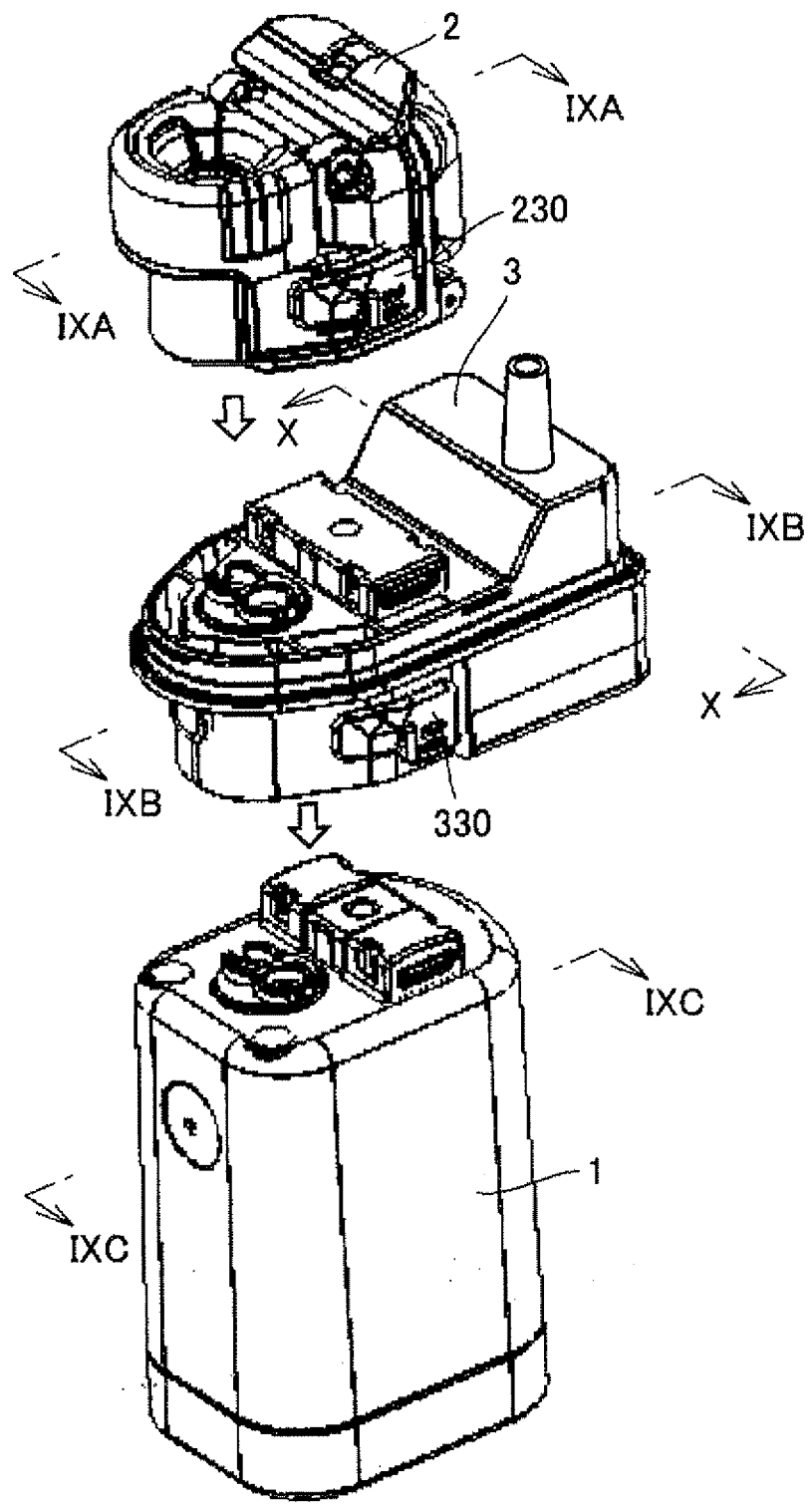

With reference to FIG. 3, the main body unit 1, the breath detection unit 3, and the atomization unit 2 can be separated from each other. In the present embodiment, the breath detection unit 3 serving as a function unit is attached (inserted) between the main body unit 1 and the atomization unit 2.

Figure 2:
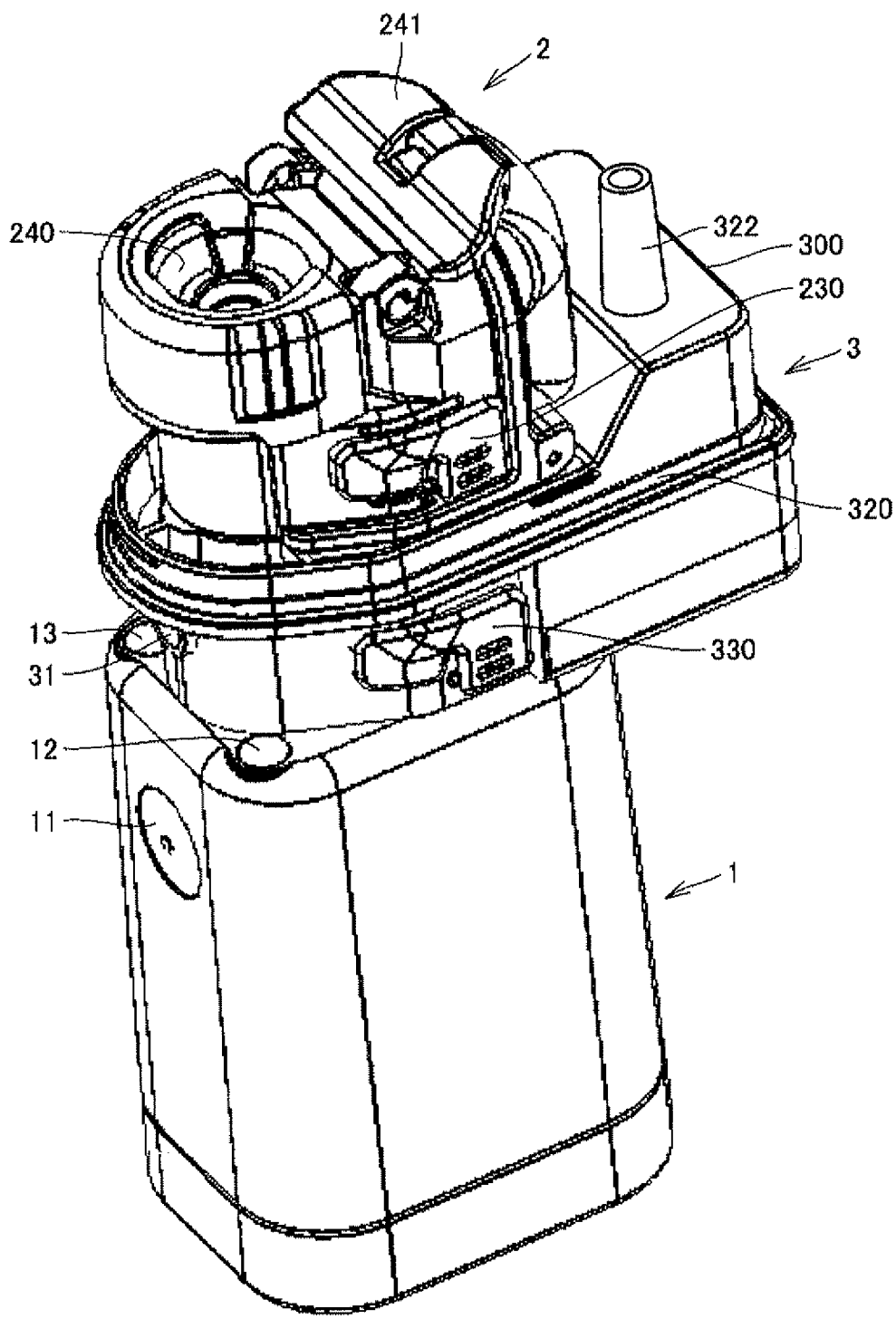

As shown in FIG. 2 and FIG. 3, the atomization unit 2 and the breath detection unit 3 may respectively include an attachment tool 230, 330 for fixing the connection state with the unit positioned immediately below. The user can manually operate such attachment tools 230, 330 to connect or separate the units.

A connection terminal (electrode) or the like is arranged on the connection surfaces of the units to enable electrical connection of the units.

Figure 4:
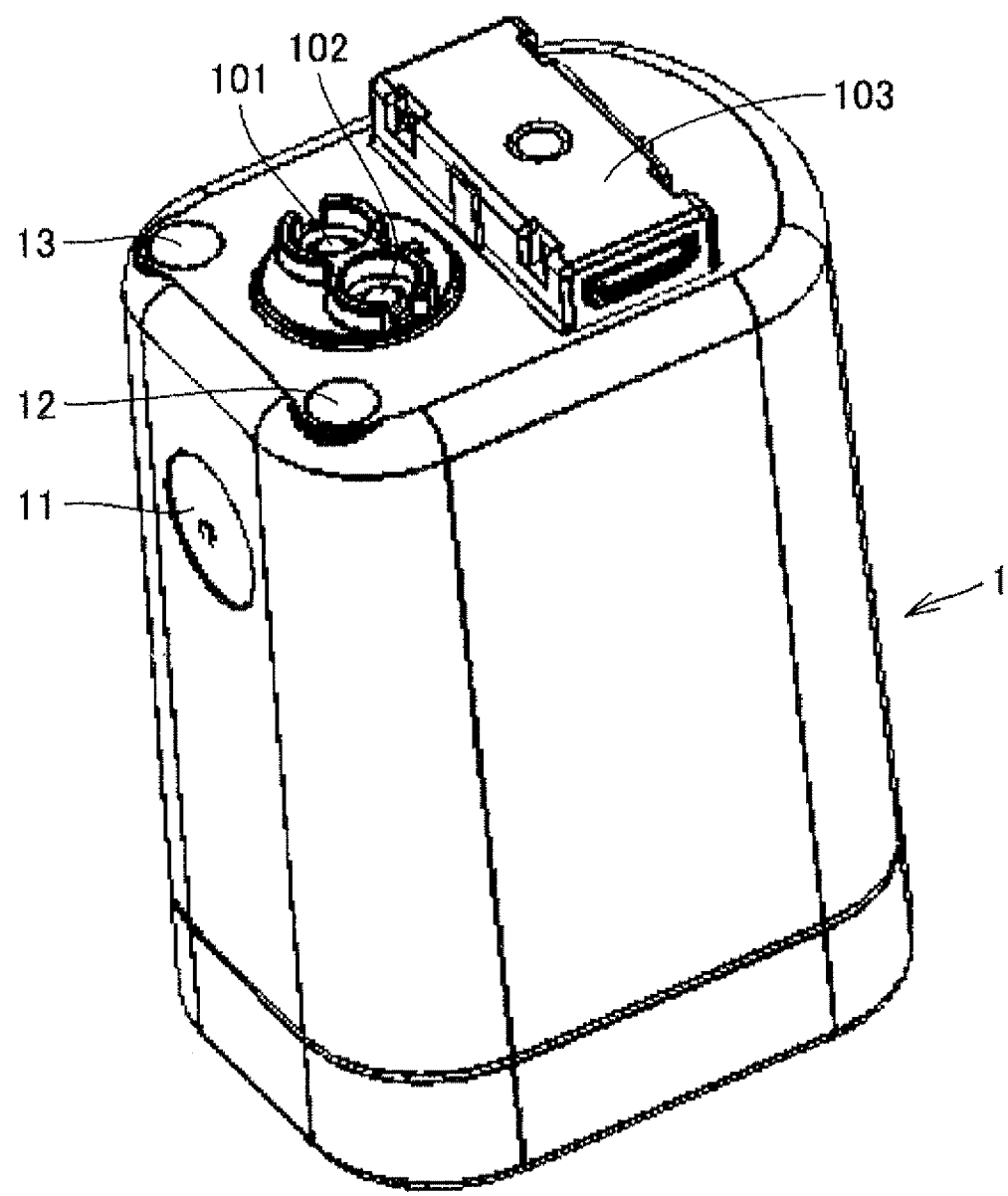

With reference to FIG. 4, connection terminals 101, 102 are arranged on the upper surface of the main body unit 1 (connecting surface with lower surface of breath detection unit 3). A projection 103 is also arranged to facilitate the attachment and positioning of the breath detection unit 3.

Figure 5:
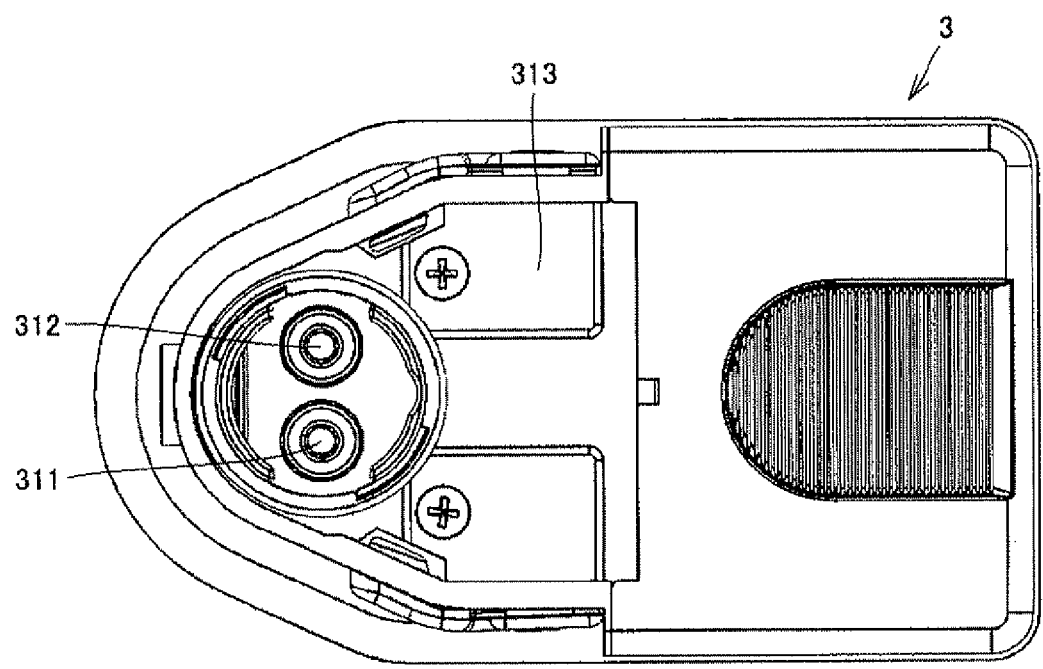

With reference to FIG. 5, connection terminals 311, 312 that can be brought into contact with the connection terminals 101, 102, respectively, of the main body unit 1 are arranged on the lower surface of the breath detection unit 3 (connecting surface with main body unit 1). A recess 313 to which the projection 103 of the main body unit 1 can be fitted is also arranged.

Figure 6:
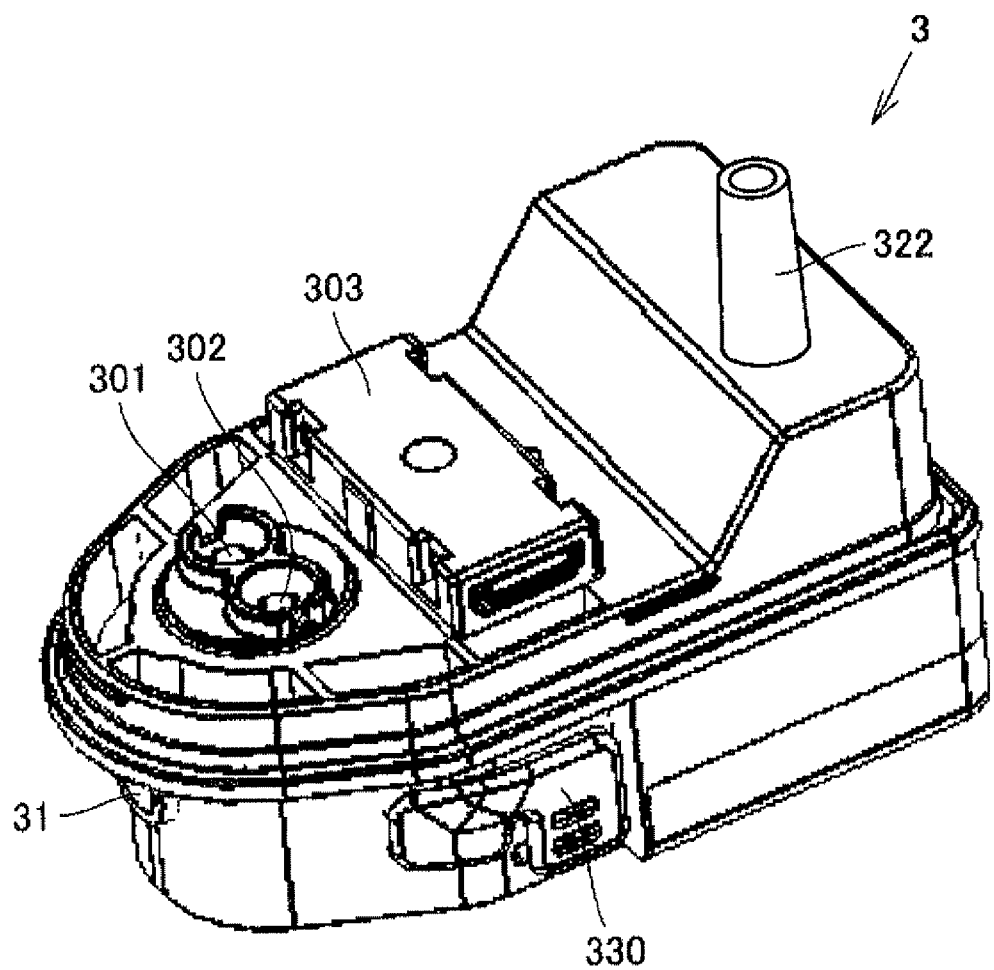

With reference to FIG. 6, connection terminals 301, 302 are arranged on the upper surface of the breath detection unit 3 (connecting surface with atomization unit 2). A projection 303 is also arranged to facilitate the attachment and positioning of the atomization unit 2.

The shapes of the connection terminals 301, 302 are similar to the connection terminals 101, 102 of the main body unit 1. The shape of the projection 303 is also similar to the projection 103 of the main body unit 1.

Figure 7:
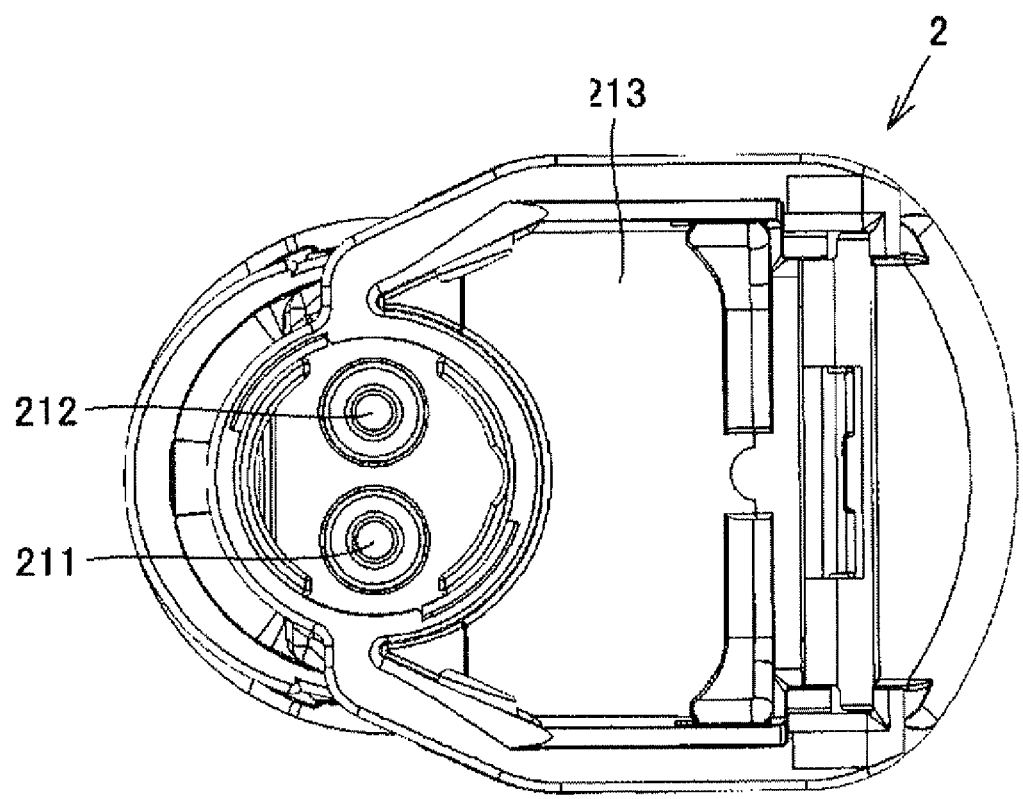

With reference to FIG. 7, connection terminals 211, 212 that can be brought into contact with the connection terminals 301, 302, respectively, of the breath detection unit 3 are arranged on the lower surface of the atomization unit 2 (connecting surface with breath detection unit 3). A recess 213 to which the projection 303 of the breath detection unit 3 can be fitted is also arranged.

The shapes of the connection terminals 211, 212 are similar to the connection terminals 311, 312 of the breath detection unit 3. The shape of the recess 213 is also similar to the recess 313 of the breath detection unit 3.

(Regarding Circuit Configuration)

Figure 8:
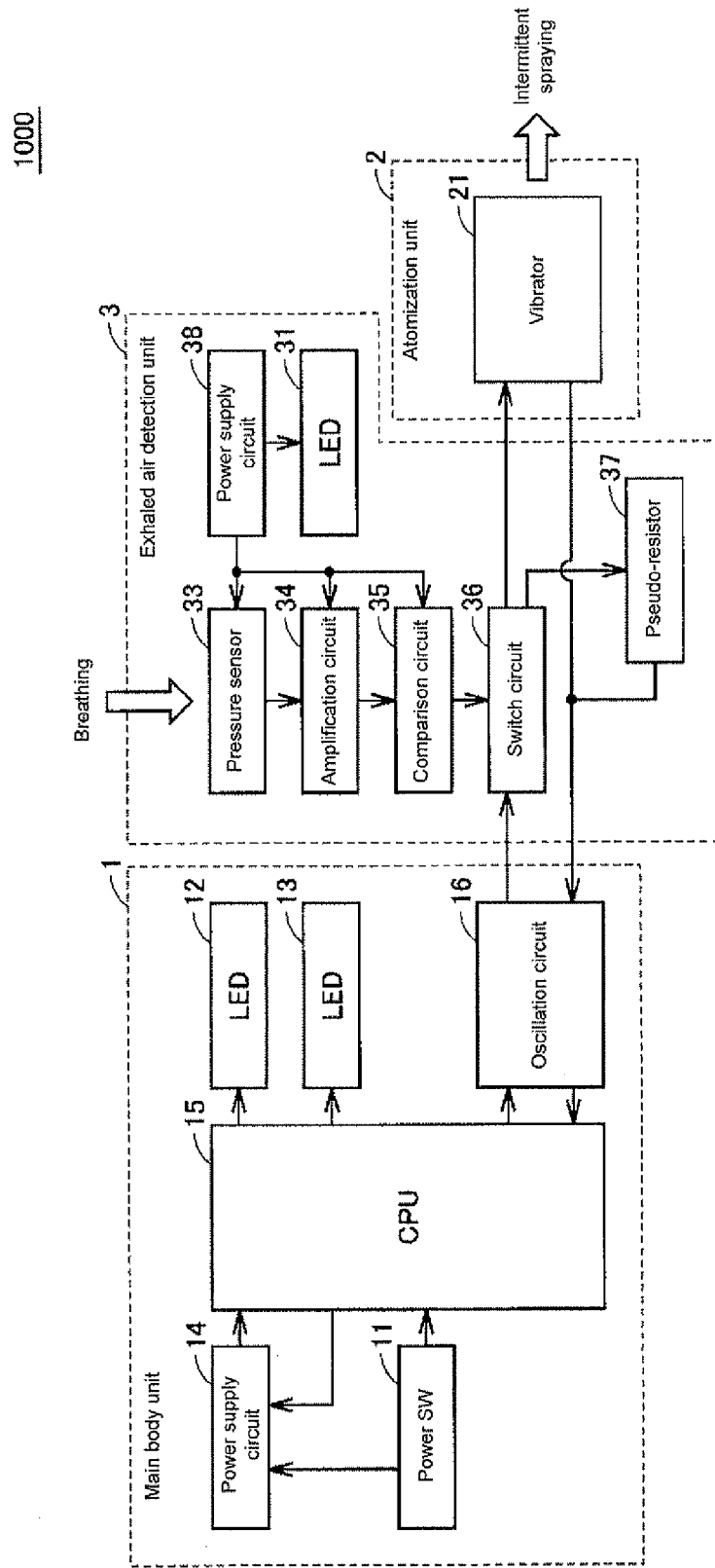

With reference to FIG. 8, the main body unit 1 includes a power supply circuit 14, a CPU (Central Processing Unit) 15, and an oscillation circuit 16, in addition to the power supply switch 11 and the LEDs 12, 13.

The power supply circuit 14 includes a battery, and supplies power to each portion of the main body unit 1. The CPU 15 controls each portion. The oscillation circuit 16 outputs an oscillation signal to the breath detection unit 3 (switch circuit 36 to be described later) based on the control signal from the CPU 15.

In the present embodiment, the oscillation signal is output for a constant time from when the power supply switch 11 is pushed. The measurement of a constant time may be carried out by a timer (not shown).

The atomization unit 2 includes a vibrator 21 driven to atomize the medicinal solution. The vibrator 21 vibrates in response to the oscillation signal.

The breath detection unit 3 includes a power supply circuit 38, a pressure sensor 33, an amplifier circuit 34, a comparison circuit 35, a switch circuit 36, and a pseudo-resistor 37, in addition to the LED 31.

The pressure sensor 33 detects air pressure involved in breathing. The detected pressure signal is output to the amplifier circuit 34. The amplifier circuit 34 amplifies the pressure signal output from the pressure sensor 33. The amplified pressure signal is output to the comparison circuit 35. The comparison circuit 35 compares the value (hereinafter referred to as "pressure value") of the pressure signal output from the amplifier circuit 34 with a reference value defined in advance, and outputs the result to the switch circuit 36. More specifically, Low signal is output if the pressure value is greater than or equal to the reference value (in exhaling), and High signal is output if the pressure value is smaller than the reference value (in inhaling).

The switch circuit 36 is configured by an FET (Field Effect Transistor). The switch circuit 36 inputs the oscillation signal output by the oscillation circuit 16 of the main body unit 1. The switch circuit 36 selects the output destination of the input oscillation signal according to the signal (High or Low) from the comparison circuit 35.

Specifically, the atomization unit 2 (vibrator 21) is selected as the output destination when the High signal is input from the comparison circuit 35. Therefore, the oscillation signal is transferred to the vibrator 21 thus vibrating the vibrator 21.at the time of inhaling. The medicinal solution is thereby sprayed from the spray port 240. On the other hand, the pseudo-resistor 37 is selected as the output destination when the Low signal is input from the comparison circuit 35. Therefore, the oscillation signal is not transferred to the vibrator 21 and thus does not vibrate the vibrator 21, and hence the medicinal solution is not sprayed from the spray port 240 at the time of exhaling.

Therefore, the breath detection unit 3 includes a configuration (pressure sensor 33 etc.) for detecting the breathing state of the user, and a configuration (comparison circuit 35 switch circuit 36, etc.) for causing the atomizing section to atomize the medicinal solution only in the case of inhaling. Therefore, according to the nebulizer 1000, even if the oscillation circuit 16 continuously outputs the oscillation signal, the medicinal solution is intermittently sprayed (only in inhaling) in the atomization unit 2. As a result, the medicinal solution can be efficiently sprayed.

Figure 9:
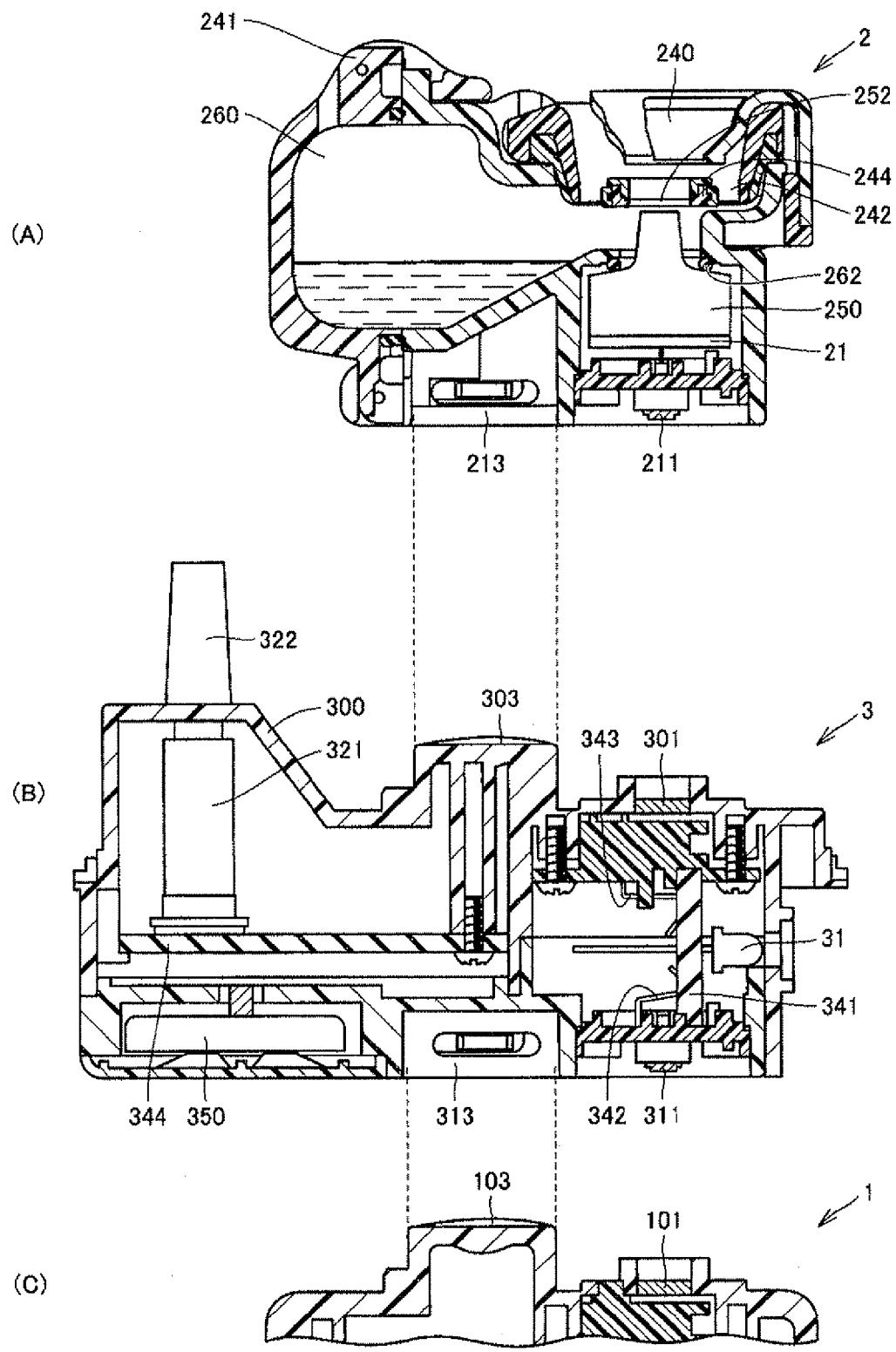

The power supply circuit 38 of the breath detection unit 3 includes a button type batter 350 (FIG. 9). The power is supplied from the power supply circuit 38 to the pressure sensor 33, the amplification circuit 34, and the comparison circuit 35. In the present embodiment, the power supply circuit 38 is also arranged in the breath detection unit 3, but power may be supplied from the power supply circuit 14 in the main body unit 1 to each section of the breath detection unit 3 when connected with the main body unit 1.

(Regarding Internal Structure of Each Unit)

One example of the internal structures of the atomization unit 2 and the breath detection unit 3 will be described with reference to FIGS. 9(A) to 9(C). FIG. 9(A) shows a cross-section of the atomization unit 2 taken along line IXA-IXA shown in FIG. 3, and FIG. 9(B) shows a cross-section of the breath detection unit 3 taken along line IXB-IXB shown in FIG. 3. FIG. 9(C) partially shows the cross-section of the main body unit 1 taken along line IXC-IXC shown in FIG. 3.

The cross section of the main body unit 1 is assumed to include the cross-section of the connection terminal 101. Similarly, the cross-section of the breath detection unit 3 includes the cross-sections of the connection terminals 301, 311, and the cross-section of the atomization unit 2 includes the cross-section of the connection terminal 211.

With reference to FIG. 9(A), the atomization unit 2 includes an ultrasonic mesh type atomization mechanism immediately under the spray port 240. The ultrasonic mesh type atomization mechanism includes a vibrator (piezoelectric element) 21, a step horn 250, and a mesh 252. The mesh 252 has a great number of microscopic holes, and is brought into contact with one end of the step horn 250 at the lower surface. The vibrator 21 is vibrated by the oscillation signal obtained from the connection terminal 211. When such vibration is propagated to the step horn 250, the medicinal solution is atomized at the contacting surface of the step horn 250 and the mesh 252. The atomized medicinal solution is vigorously blown out from the microscopic holes to the spray port 240.

A liquid retaining portion 242 for retaining the droplet medicinal solution or drool of the user is formed at the circumferential edge of the spray port 240. The medicinal solution or the drool retained in the liquid retaining portion 242 is partitioned by a partition plate 244 so as not to mix into the mesh 252 positioned on the inner side.

Furthermore, the medicinal solution storage section 260 for storing the medicinal solution is formed inside the atomization unit 2. The medicinal solution stored in the medicinal solution storage section 260 is completely atomized by being tilted at the time of use. The water tight structure is provided by an O ring 262 so that the medicinal solution does not flow out into the device.

The recess 213 formed at the lower part of the atomization unit 2 is fitted to the projection 303 of the breath detection unit 3. When the recess 213 and the projection 303 are fitted, the connection terminal 211 is brought into contact with the connection terminal 301 of the breath detection unit 3 so as to be in an electrically conductive state.

With reference to FIG. 9(B), the breath detection unit 3 is installed with a sheet metal terminal 343 electrically connected to the connection terminal 301, and a sheet metal terminal 342 electrically connected to the connection terminal 311. Since such sheet metal terminals 342, 343 are electrically connected to the substrate 341, the main body unit 1 and the atomization unit 2 can be electrically conducted. Therefore, the substrate 341 and the sheet metal terminals 342, 343 serve as relay portions for electrically connecting the main body unit 1 and the atomization unit 2.

The breath detection unit 3 includes a substrate 344 incorporated with the above described circuits (at least one part of power supply circuit 38, amplification circuit 34, comparison circuit 35, switch circuit 36). A power line (not shown) is connected from the substrate 341 to the substrate 344, so that the substrates 341, 344 are electrically connected.

The substrates 341, 344 and the sheet metal terminals 342, 343 are incorporated in the housing 300.

A configuration example of the breath detection unit for detecting the breathing state of the user will now be described with further reference to FIG. 10.

The second tube portion 322 arranged in a projection manner from the housing 300 takes in gas (exhaled air of user) from the outside, or discharges the internal gas. The gas that passed through the second tube portion 322 is flowed into the first tube portion 321 and guided to the pressure sensor 33 arranged on the substrate 344. The pressure sensor 33 detects the breathing state by detecting the air pressure in the first tube portion 321.

In the present embodiment, the breath detection unit includes the first tube portion 321, the second tube portion 322, and the pressure sensor 33. The configuration of the breath detection unit is not limited to such form.

With reference to FIGS. 9(B) and 9(C), the recess 313 formed at the lower part of the breath detection unit 3 is fitted to the projection 103 of the main body unit 1. When the recess 313 and the projection 103 are fitted, the connection terminal 311 is brought into contact with the connection terminal 101 of the main body unit 1 so that they are in a conductive state.

(Regarding Operation of Nebulizer at the Time of Use)

The operation of the nebulizer 1000 at the time of use will now be described with reference to FIG. 10, the cross-sectional views of FIG. 11 and FIG. 12, and FIG. 13. FIG. 11 and FIG. 12 show cross-sections of the nebulizer 1000 (excluding main body unit 1) taken along lines XI, XII-XI, XII shown in FIG. 1. The cross-sections in FIG. 11 and FIG. 12 both include the cross-sections shown in FIGS. 9(A) and 9(B).

Figure 13:
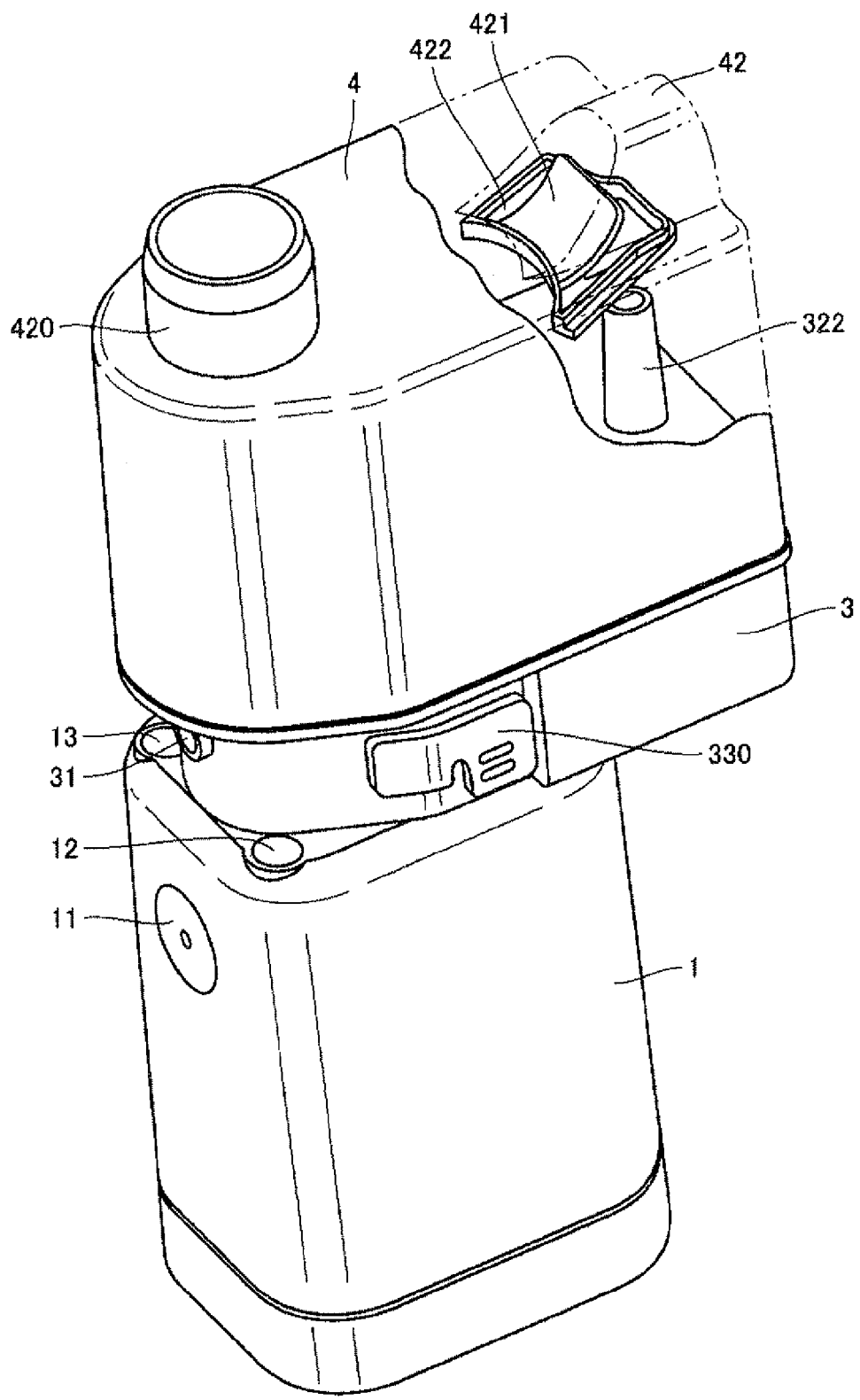

With reference to FIG. 13, an exhaled air valve 421 for preventing the gas from the outside from flowing in is arranged at the lower part of the ventilating portion 42 of the cover unit 4. The exhaled air valve 421 is attached to the lower part of the ventilating portion 42 of the cover unit 4 through an attachment member 422, and is opened and closed by the air pressure in the cover unit 4. As shown in FIG. 13, the tubular portion 420 for attaching the mouth piece 41 is arranged at the upper part of the cover unit 4.

Figure 10:
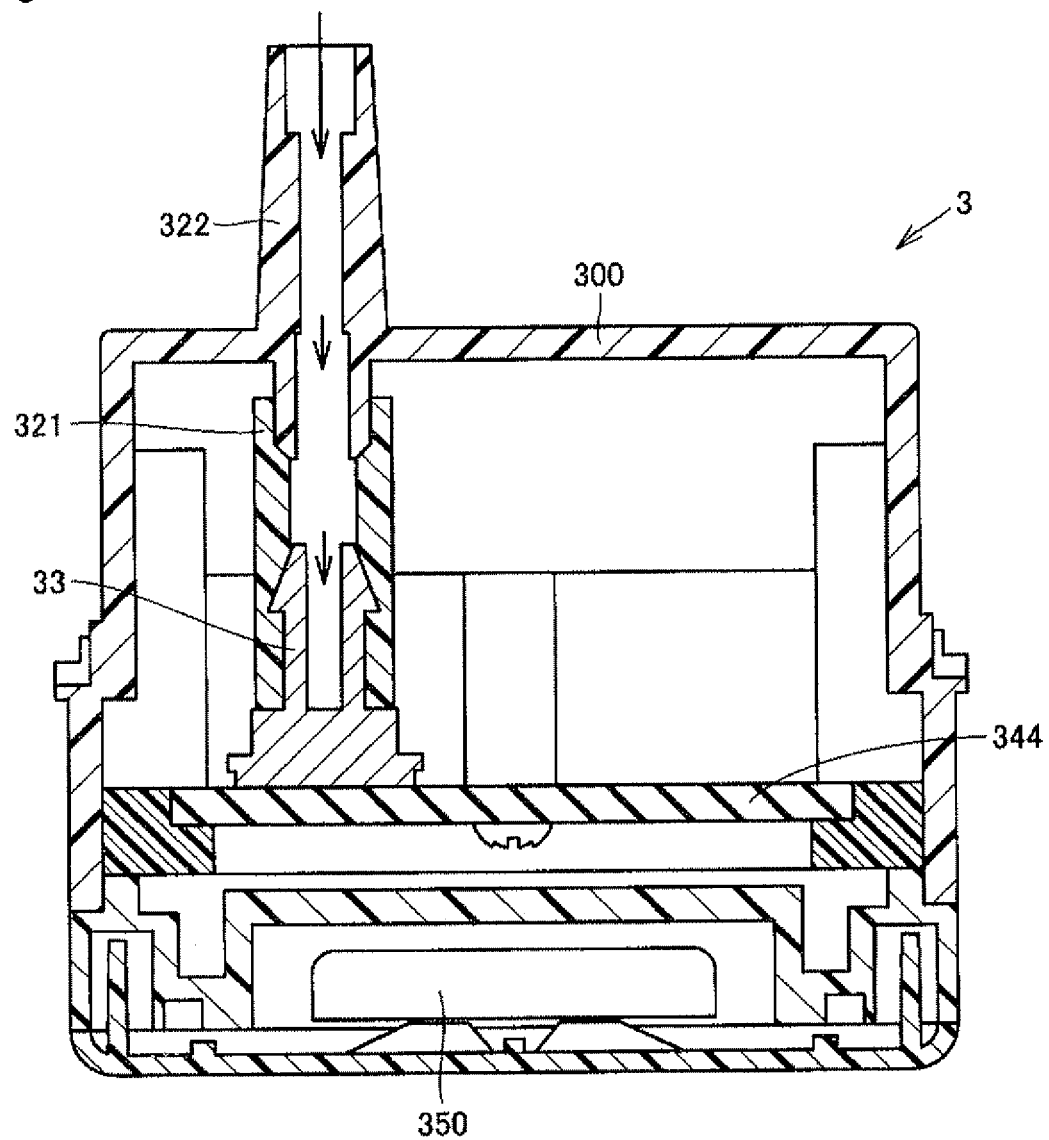
Figure 11:
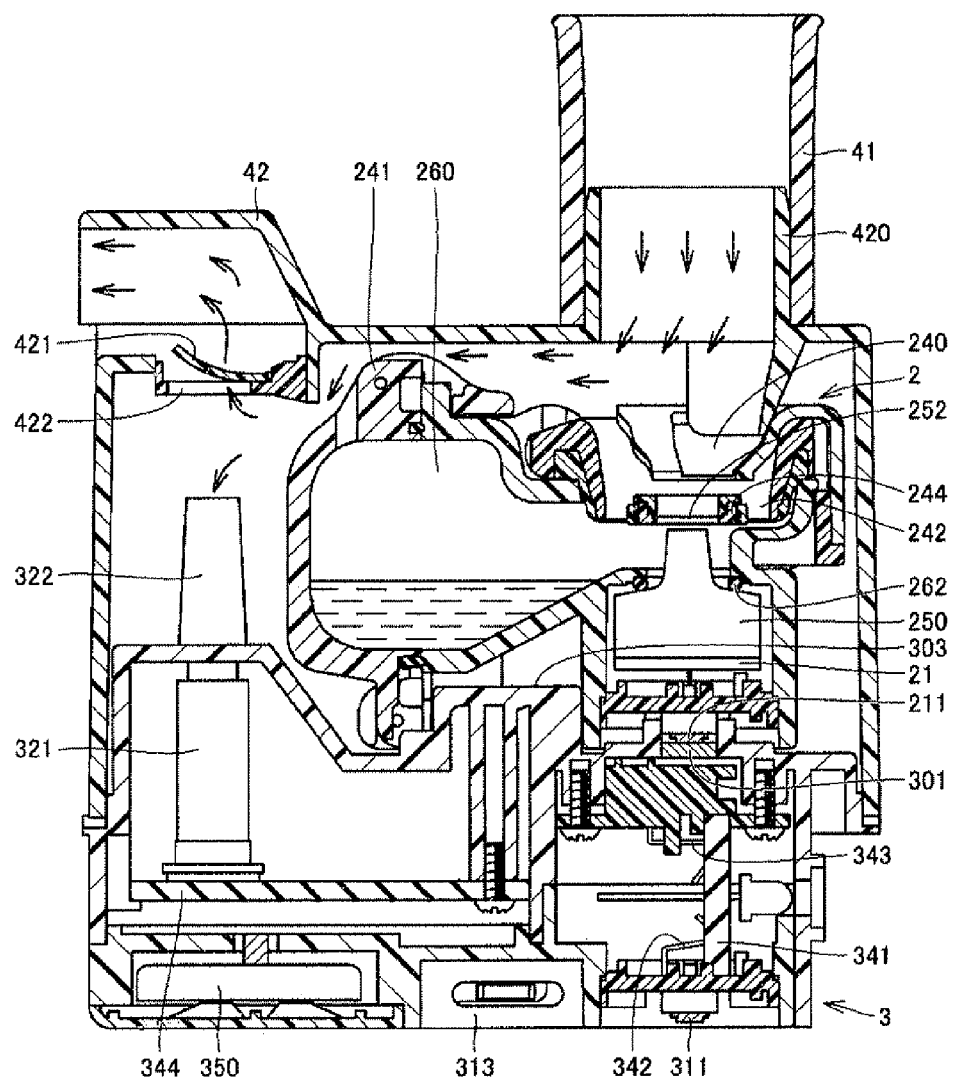
Figure 12:
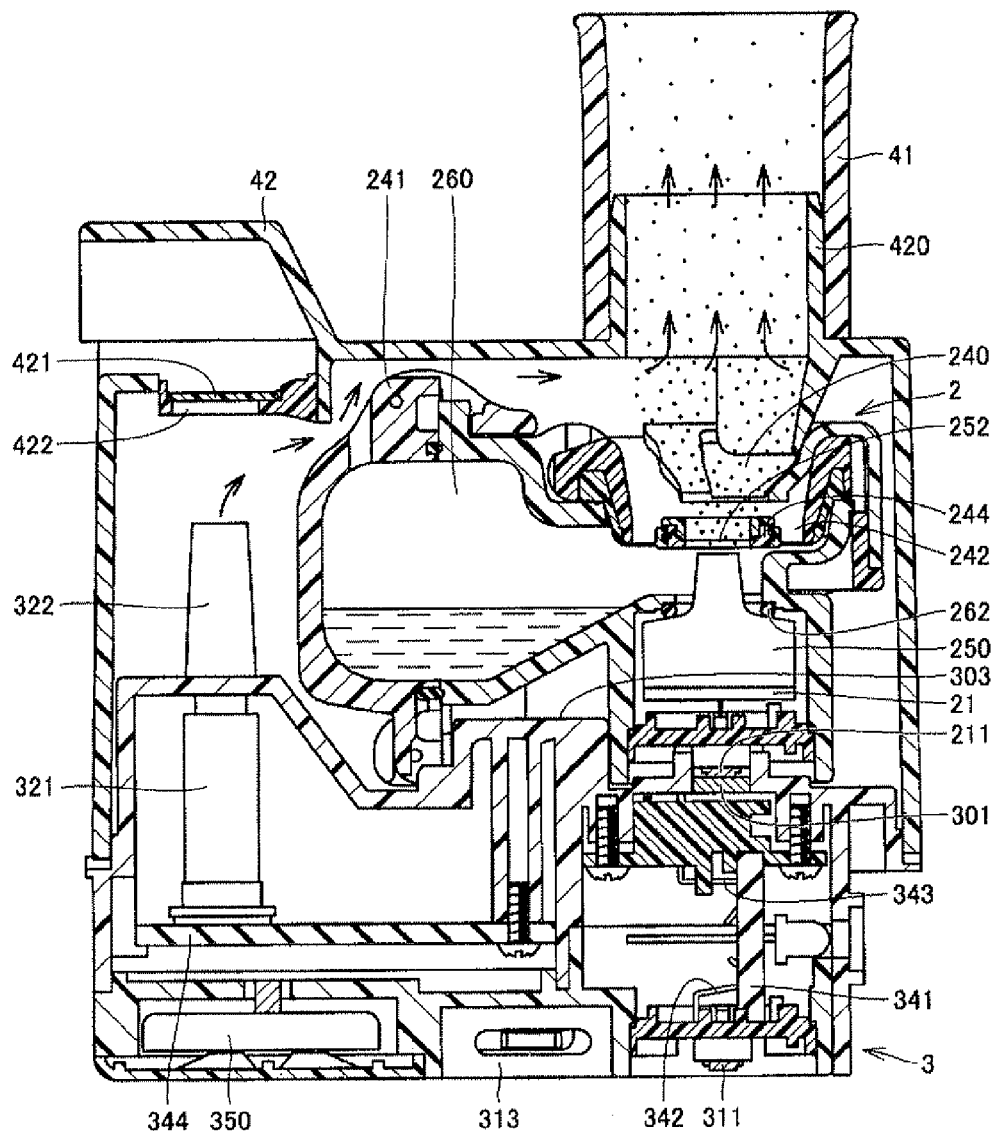

First, with reference to FIG. 10 and FIG. 11, the operation of the nebulizer 1000 in exhaling (case in which user exhales with the mouth piece 41 held at the mouth) will now be described.

When the user exhales while holding the mouth piece 41 at the mouth, the gas (breath), flows into the cover unit 4 from the tubular portion 420. The gas that flowed in then flows into the air path configured by the first and second tube portions 321, 322, as shown with arrows in FIG. 11. Further, the gas that flowed in also pushes the exhaled air valve 421 upward. The exhaled air valve 421 is thus in an open state, and the gas in the cover unit 4 flows out to the outside through the exhaled air valve 421 and the ventilating portion 42.

In such exhaling, the pressure sensor 33 outputs a voltage higher than the reference voltage since the gas flows into the air path. Therefore, the output of the comparison circuit 35 is Low signal. In such a case, the oscillation signal is output to the pseudo-resistor 37. Thus, the oscillation signal does not reach up to the connection terminal 301 (302), and the vibrator 21 is not vibrated. Therefore, at the time of exhaling, the medicinal solution in the medicinal solution storage section 260 is not sprayed.

Next, with reference to FIG. 10 and FIG. 12, the operation of the nebulizer 1000 at the time of inhaling (case in which user inhales while holding the mouth piece 41 at the mouth) will now be described.

When the user inhales while holding the mouth piece 41 at the mouth, the exhaled air valve 421 is closed. The flow of the gas from the ventilating portion 42 into the cover unit 4 is thus suppressed. The gas inside the cover unit 4 up to this point is then taken up, and hence the gas flows out from the air path.

In such inhaling, the pressure sensor 33 outputs a voltage lower than the reference voltage since the gas flows out from the air path. Therefore, the output of the comparison circuit 35 is High signal. In such a case, the oscillation signal is transmitted to the substrate 341 through a power line (not shown). The oscillation signal is then output from the substrate 341 to the connection terminal 301 (302) through the sheet metal terminal 343. Thus, the oscillation signal is transmitted to the vibrator 21 and the vibrator 21 is vibrated since the connection terminals 301, 302 of the breath detection unit 3 and the connection terminals 211, 212 of the atomization unit 2 are in a conductive state at the time of use. As a result, the gas containing the medicinal solution atomized by the mesh 252 flows into the mouth of the user through the mouth piece 41.

(Regarding Configuration of Nebulizer when Function Unit is not Attached)

The configuration of the nebulizer when the function unit, that is, the breath detection unit 3 is not attached will now be described.

Figure 14:
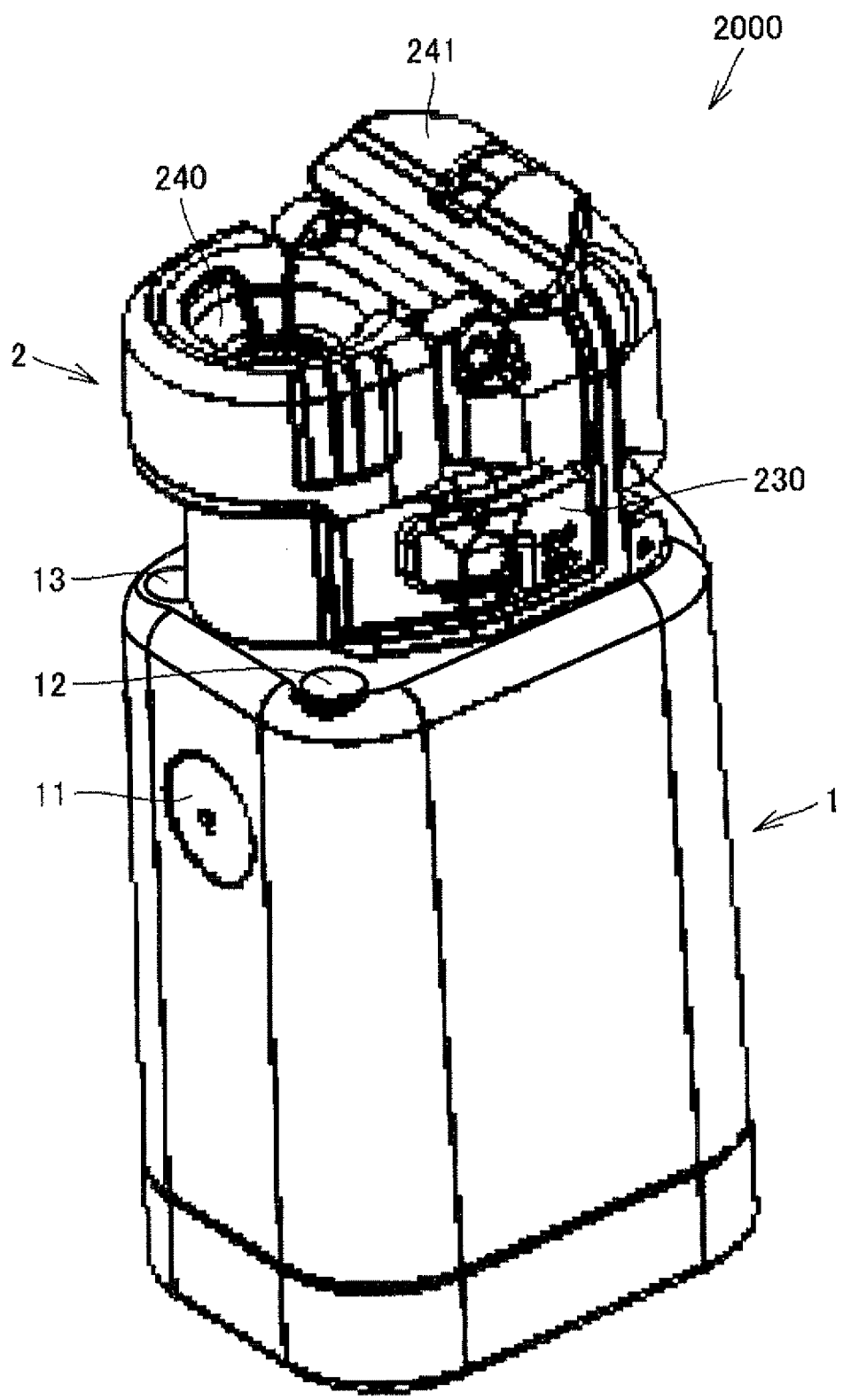

With reference to FIG. 14, a nebulizer 2000 does not include the breath detection unit 3, and is configured by the main body unit 1 and the atomization unit 2 separable from the main body unit 1, The nebulizer 2000 can be referred to as a device for realizing only the basic functions of the nebulizer. In the present embodiment, such nebulizer is referred to as "nebulizer of basic specification". The nebulizer 2000 may be similar to the configuration of the mesh type nebulizer NE-U22 manufactured and sold by the applicant.

When using the nebulizer 2000, an inhale mask portion (not shown) for assisting inhalation, or the like may be attached so as to cover the atomization unit 2 in place of the cover unit 4 described above.

Figure 15:
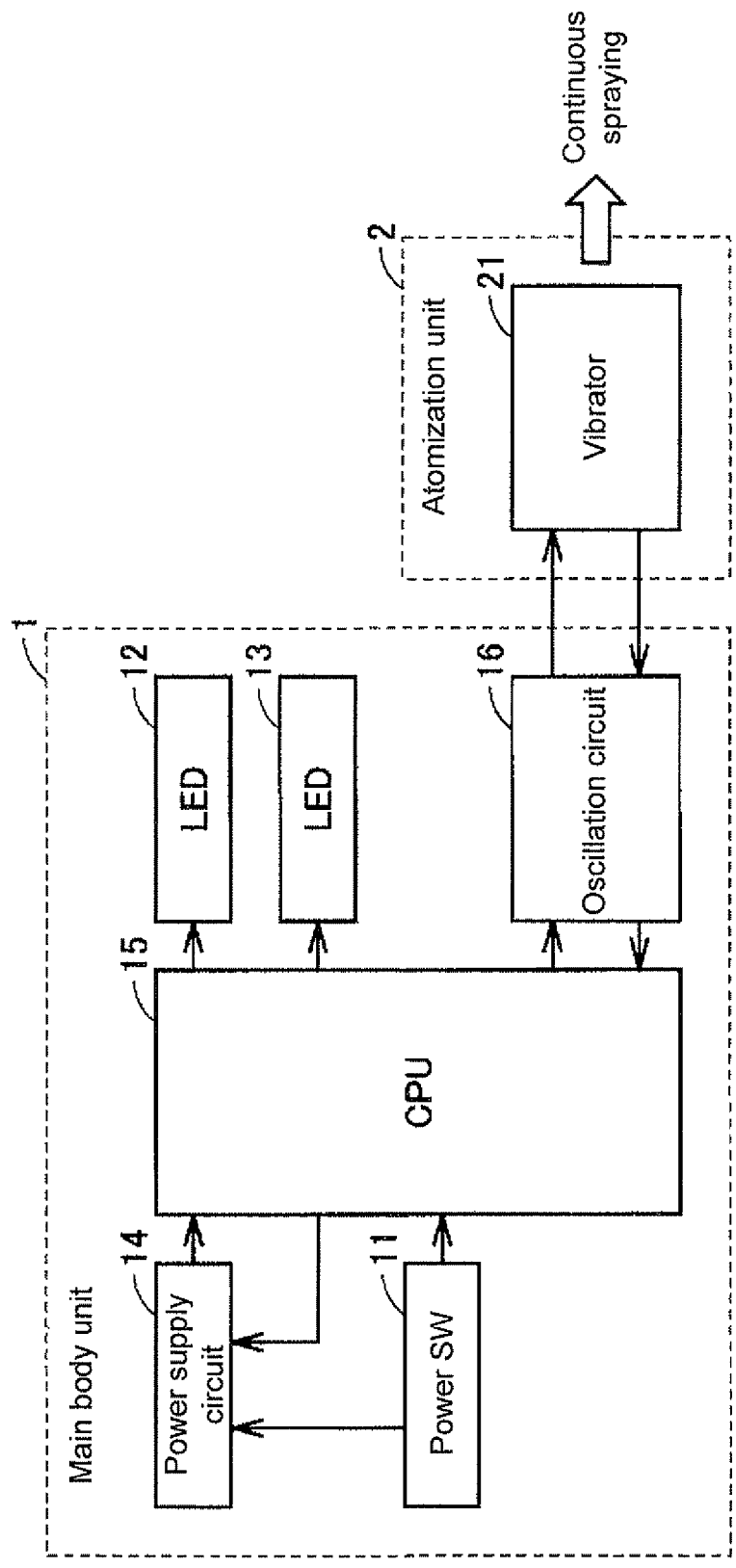

With reference to FIG. 15, in the nebulizer 2000, when the oscillation circuit 16 of the main body unit 1 outputs the oscillation signal, the oscillation signal is transmitted to the vibrator 21 of the atomization unit 2 as is. Therefore, when the oscillation signal is continuously output, the medicinal solution is continuously sprayed regardless of the breathing state of the user.

Figure 16:
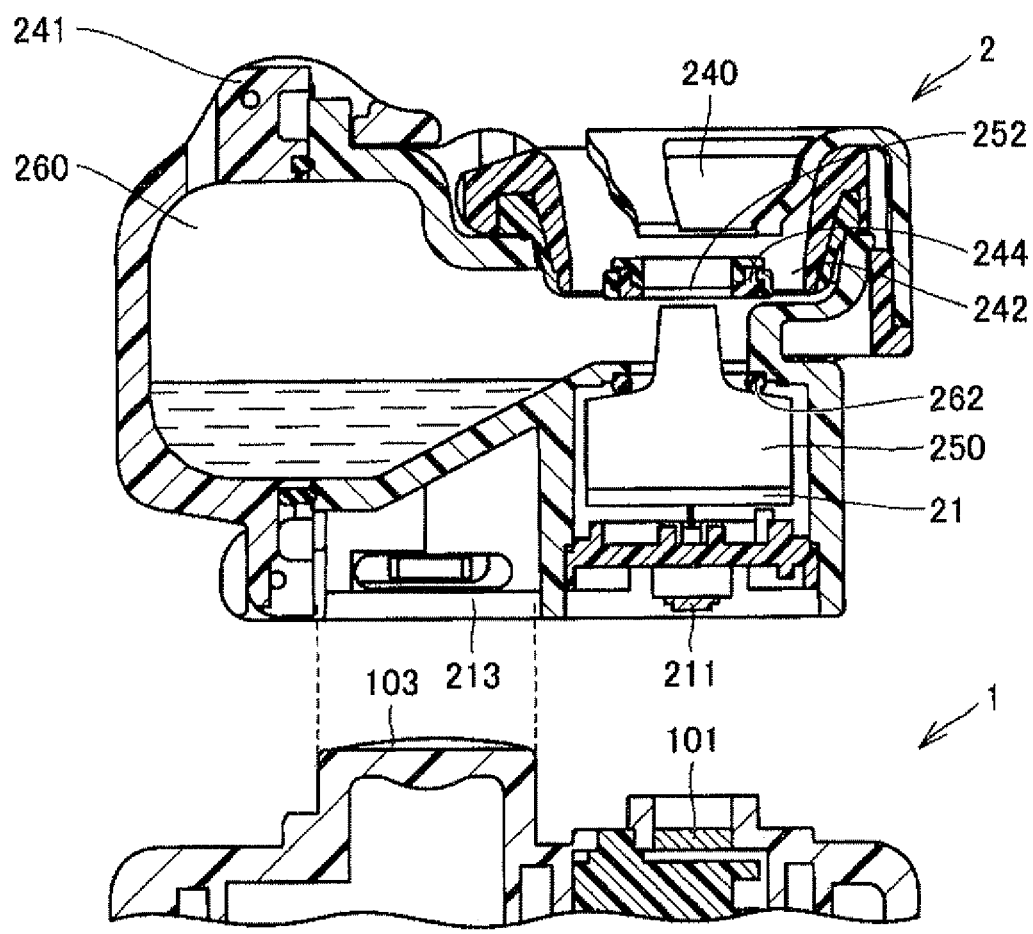

With reference to FIG. 16, in the nebulizer 2000, the connection terminal 101 (102) and the projection 103 at the upper surface of the main body unit 1 can be connected to the connection terminal 211 (212) and the recess 213, respectively, at the lower surface of the atomization unit 2.

As described above, the main body unit 1 and the atomization unit 2 can be connected physically and electrically since the shapes of the connection terminals 101, 102 and the projection 103 at the upper surface of the main body unit 1 are similar to the shapes of the connection terminals 301, 302 and the projection 303 at the upper surface of the breath detection unit 3.

The nebulizer 2000 of the present embodiment has been described as a device for realizing only the basic function, but is not limited to a device for realizing only the basic function as long as it is a nebulizer in which two units are separable.

That is, another configuration capable of realizing the additional function other than the basic function of atomizing the medicinal solution may be provided to at least one of the main body unit 1 and the atomization unit 2. This case, however, is to be realized under the condition that the device does not become large as a result of including the other configuration.

Second Embodiment

A second embodiment of the present invention will now be described.

In the first embodiment, the breath detection unit is adopted as a function unit that can be attached and detached to the nebulizer (main body unit and atomization unit) of basic specification, but a power control unit for controlling the intensity of the spray is adopted in the present embodiment.

In the present embodiment as well, the configuration and the operation other than the power control unit are basically similar to the nebulizer 1000 of the first embodiment. Therefore, only the portion different from the first embodiment will be described below.

Figure 17:
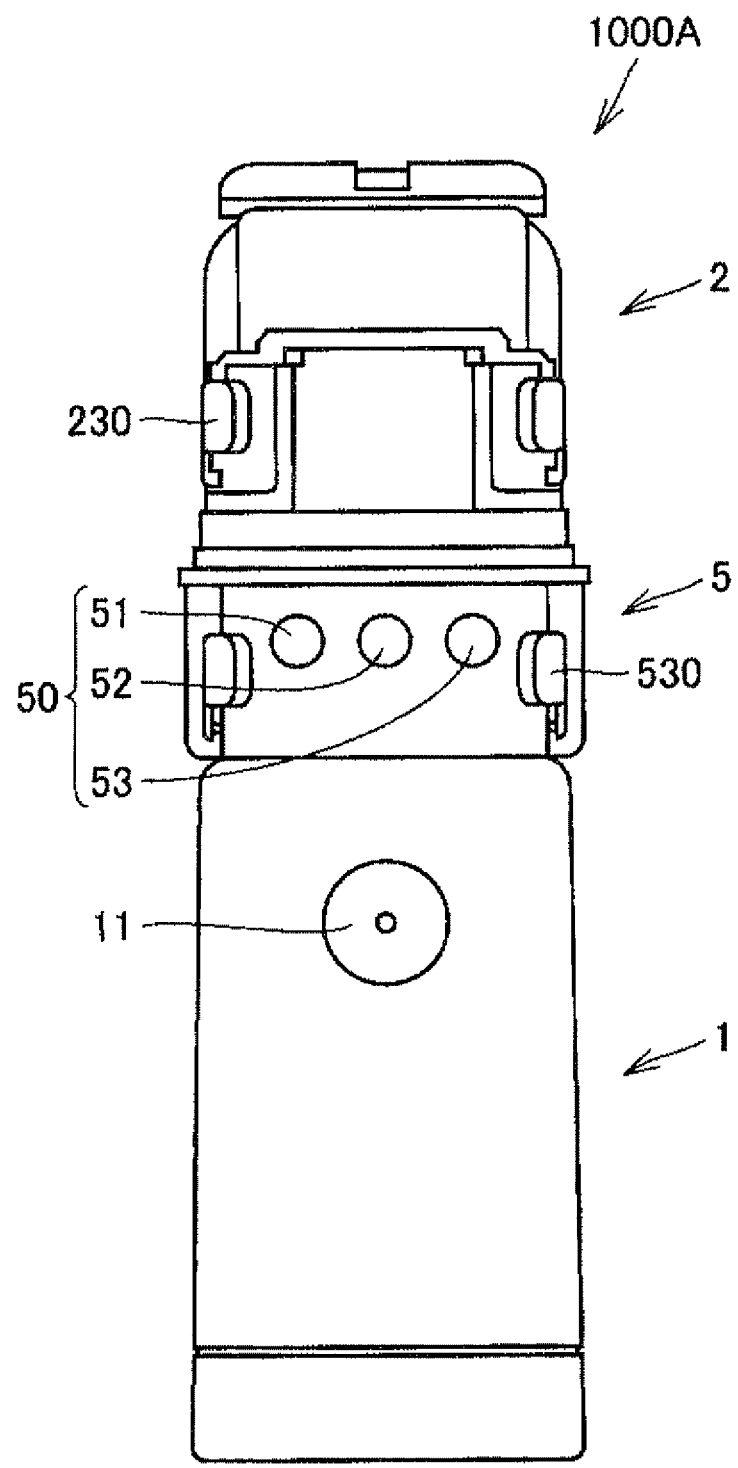

With reference to FIG. 17, a nebulizer 1000A according to the present embodiment includes the main body unit 1, the atomization unit 2, and a power control unit 5 that can be attached between the units.

The power control unit 5 has an operating section 50 to be operated by the user to adjust the intensity of the spray at the front surface. The operating section 50 includes three switches for receiving the instruction of intensity of three stages, that is, a strong (High setting) switch 51, a normal switch 52, and a weak (Low setting) switch 53. The normal switch 52 may not be arranged.

Figure 18:
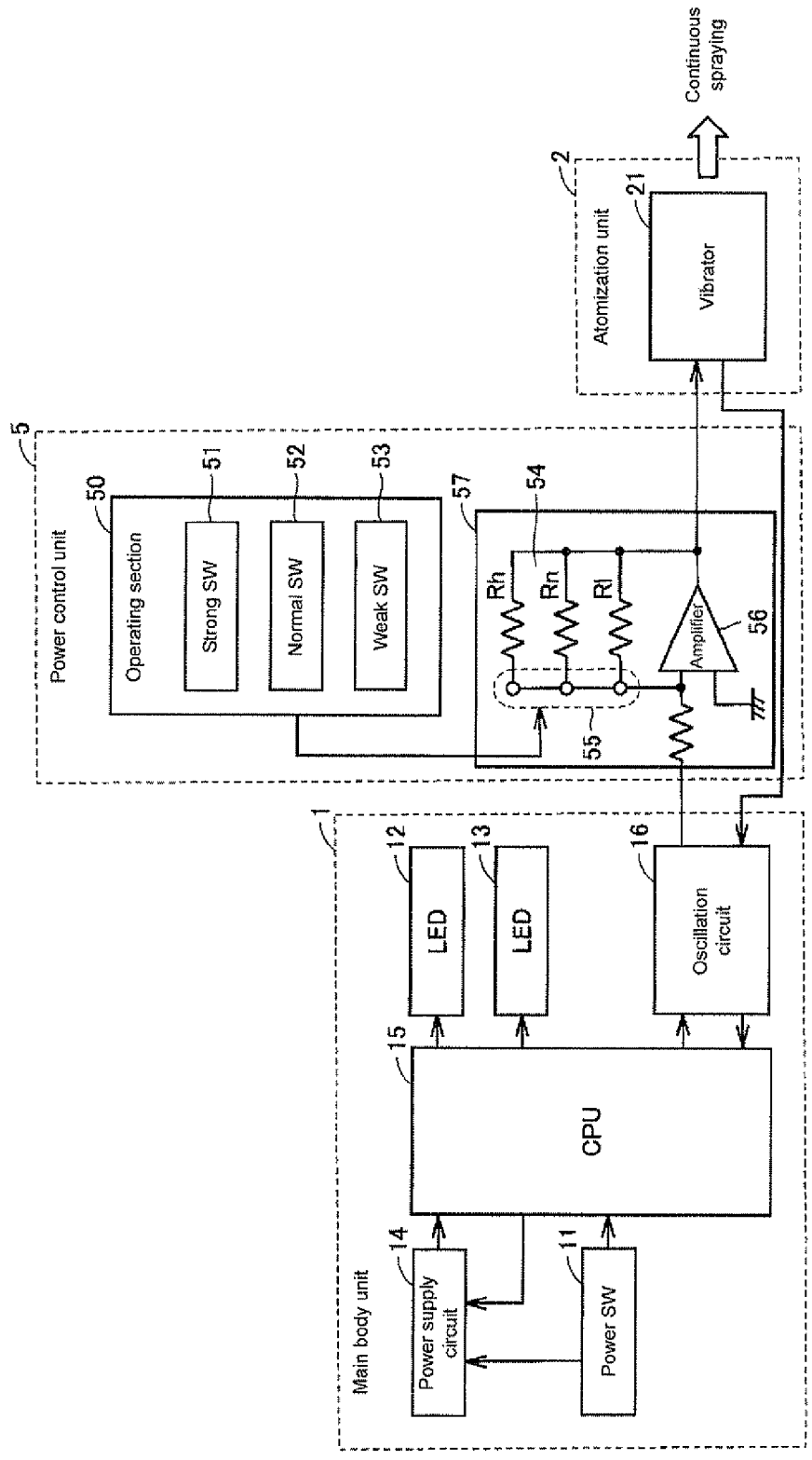

FIG. 18 is a block diagram showing one example of a circuit configuration of the nebulizer 1000A. The configurations of the main body unit 1 and the atomization unit 2 are similar to the first embodiment.

The power control unit 5 further includes an amplitude adjusting section 57 for adjusting the spray amount per unit time by the atomizing section (vibrator 21, step horn 250, mesh 252), in addition to the operating section 50.

The amplitude adjusting section 57 receives the oscillation signal from the oscillation circuit 16 of the main body unit 1, and amplifies/damps the received oscillation signal according to the instruction from the user. That is, when the user pushes the strong switch 51, the received oscillation signal is amplified. When the user pushes the weak switch 53, the received oscillation signal is damped. When the user pushes the normal switch 52, the adjustment of the amplitude is not carried out.

The amplitude adjusting section 57 includes a variable resistor 54, a switch terminal 55, and an operational amplifier 56 to realize the above function. When the user pushes one of the switches, one of the three switch terminals 55 is selected in accordance with the pushed switch.

The amplitude adjusting section 57 outputs the oscillation signal, in which the amplitude is adjusted, to the vibrator 21. Spray amount per constant time by the atomizing section in the vibrator 21 becomes greater as the amplitude of the transmitted oscillation signal is larger. Thus, if the output time of the oscillation signal is not fixed (constant time) and a constant amount of medicinal solution is to be atomized, the inhaling time of the medicine can be reduced as a result. Therefore, according to the present embodiment, the user can adjust the spray amount or the inhaling time.

As a result, the appropriate spray amount or inhaling time can be selected according to the property (viscosity) of the medicine, the age of the user, the body condition of the user, or the like.

For example, the medicinal solution having high viscosity tends to be hard to spray due to the structure of the atomizing section (in particular, mesh 252) compared to when this is not the case. The appropriate spray amount can be realized by setting to High setting (strong switch 51) when the viscosity of the medicinal solution stored in the medicinal solution storage section 260 is high, and to Low setting (weak switch 53) when the viscosity is low.

The spray amount suited to the user can be realized by setting to High setting if the user is an adult and to Low setting if the user is a child or an elderly.

The user can select an optimum inhaling time according to the condition of the user and the feeling at the time by setting to High if the user desires to inhale the medicine in a short period of time and setting to Low if the user desires to inhale slowly.

If the state of the patient (course of treatment, status of improvement) changes or if there is a need to administer a new medicine, the appropriate spray amount or the inhaling time can be realized with the High setting and the Low setting.

The configuration (configuration of relay portion) in which the power control unit 5 enables an electrical connection with the main body unit 1 and the atomization unit 2 may be similar to the breath detection unit 3.

A projection (not shown) of the same shape as the projection 303 of the breath detection unit 3 is arranged on the upper surface of the power control unit 5, and a recess (not shown) of the same shape as the recess 313 of the breath detection unit 3 is arranged on the lower surface of the power control unit 5.

In the present embodiment, the spray amount and the inhaling time can be adjusted by adjusting the amplitude of the oscillation signal, but the frequency of the oscillation signal may be adjusted.

Third Embodiment

A third embodiment of the present invention will now be described.

In the present embodiment, an extension cord unit is adopted as a function unit that can be attached and detached to the nebulizer (main body unit and atomization unit) of basic specification.

In the present embodiment as well, the configuration and the operation other than the extension cord unit are basically similar to the first embodiment. Therefore, only the portion different from the first embodiment will be described below.

Figure 19:
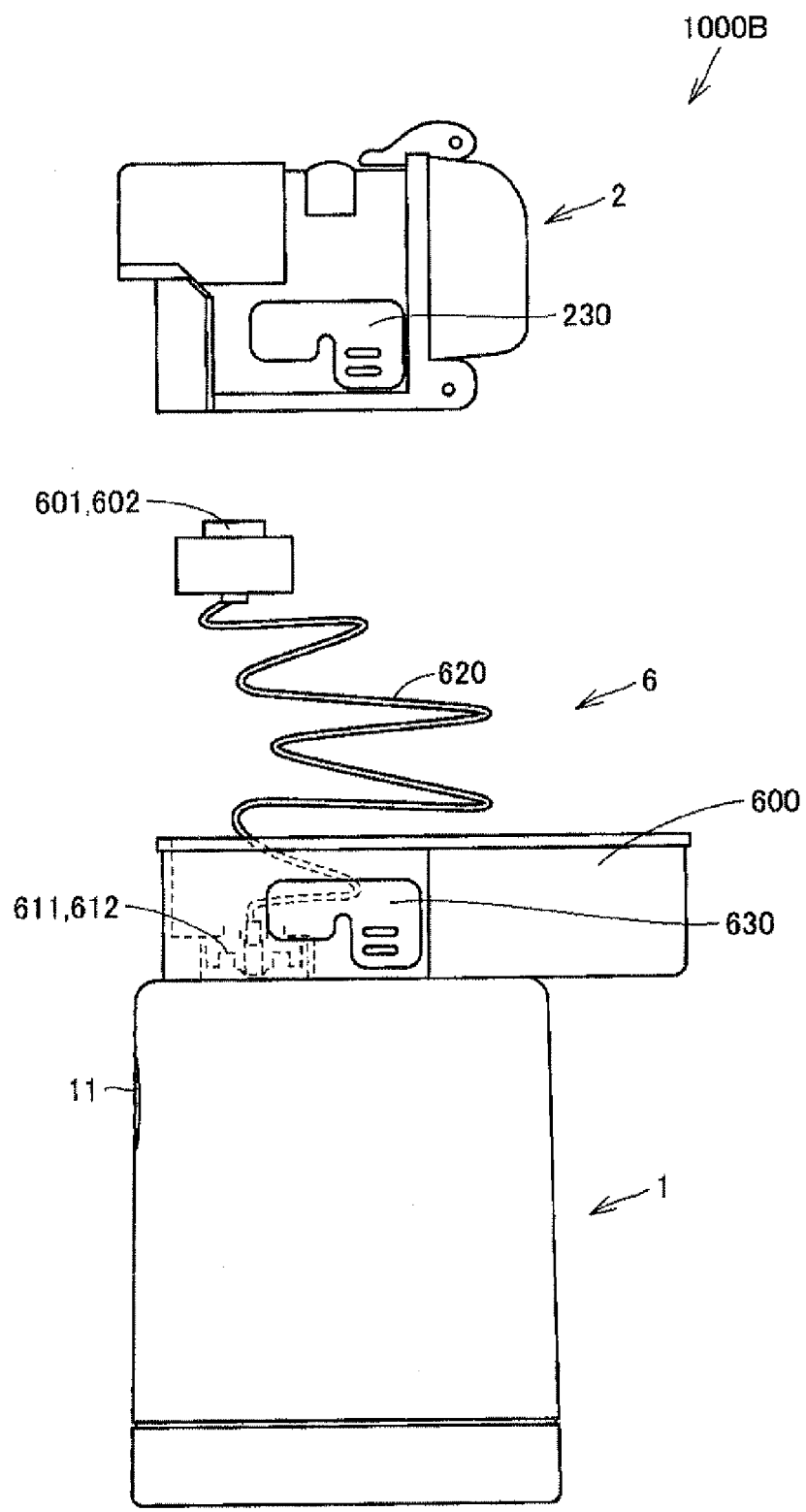

With reference to FIG. 19, a nebulizer 1000B according to the present embodiment includes the main body unit 1, the atomization unit 2, and an extension cord unit 6 that can be attached between the units.

The extension cord unit 6 includes an extension cord 620, and a housing 600 with an accommodating portion for accommodating the extension cord 620.

Connection terminals 611, 612 for connecting with the connection terminals 101, 102 of the main body unit 1 are arranged on the lower surface of the housing 600. One end of the extension cord 620 is connected to the connection terminals 611, 612. The other end of the extension cord 620 is connected to the connection terminals 601, 602.

The connection terminals 611, 612 have a shape similar to the connection terminals 311, 312 of the breath detection unit 3. The connection terminals 601, 602 have a shape similar to the connection terminals 301, 302 of the breath detection unit 3. Therefore, the extension cord unit 6 can electrically connect the main body unit 1 and the atomization unit 2 even if they are separated. The extension cord unit 6 serves as a relay portion described in the first and second embodiments.

According to the nebulizer 1000B of the present embodiment, use can be made by gripping the atomization unit 2 (or inhaling mask portion (not shown)) while placing the main body unit 1 on the table. The patient thus can easily inhale while lying down. Furthermore, even users with weak grip strength can inhale the medicine on his/her own.

<Effects by First to Third Embodiments>

Therefore, according to the first to third embodiments of the present invention, the function unit (breath detection unit, power control unit) for changing the spray state, or the function unit (extension cord unit) for changing the using method can be inserted to the nebulizer of basic specification. The additional function suited to the user and the properties of the medicine thus can be easily added to the basic function of atomizing the medicinal solution.

Therefore, the user merely needs to additionally purchase the function unit that realizes the desired additional function if the user already owns the nebulizer of basic specification. The vibrator and the mesh of the atomization unit are usually expensive. Therefore, the financial burden of the user can be alleviated by adding the function unit to the nebulizer of basic specification. As a result, the nebulizer owned by the user can be efficiently used.

Furthermore, only the (necessary) function suited to the user can be added to the nebulizer of basic specification. Therefore, the device can be miniaturized compared to when a plurality of additional functions is loaded in the nebulizer main body (when separation of units is not possible).

Furthermore, the function that used to be necessary may become unnecessary due to change in the state of the patient (course of treatment, status of improvement). According to the present embodiment, the function unit that is no longer necessary can be detached any time, which enhances the convenience of the user.

Furthermore, even if drawbacks occur in the function unit, only the function unit may be sent for repair or may be changed. As a result, the burden of the user can be alleviated compared to when sending the entire nebulizer for repair. It is also convenient for the manufacturing companies as minimal changing is merely required.

Moreover, the user can use the nebulizer of basic specification even while the function unit is being repaired. Thus, the drawback in that the nebulizer cannot be used even when a necessity to inhale the medicine urgently arises at the time of the attack can be resolved.

Furthermore, there is a case of using the nebulizer at home or in the hospital, and a case of carrying around the nebulizer to inhale at the time of an emergency. The desired function unit is inserted and used in the former case, whereas only the nebulizer of basic specification can be carried around in the latter case. As a result, the user himself/herself can use the nebulizer in various forms according to the usage situation.

Furthermore, the manufacturing companies can manufacture and sell various function units as single bodies.

<Variant>

The function unit is not limited to the examples shown in the first to third embodiments. The function unit may realize other additional functions as long as it includes at least the relay portion (configuration for electrically connecting the main body unit and the atomization unit) as described in the first embodiment.

For example, a unit for detecting the amplitude of the oscillation signal at the time of no-adjustment and adjusting the amplitude of the oscillation signal according to the detected amplitude may be provided as a function unit for changing the spray state of the atomization unit. The impedance of the vibrator sometimes changes according to the type of medicinal solution or drought. The change in impedance influences the oscillation signal. Therefore, if the amplitude of the oscillation signal at the time of no-adjustment is smaller than the reference value by greater than or equal to a predetermined value, the amplitude of the oscillation signal may be amplified. This is because, in such a case, the medicinal solution to be atomized is assumed to have a viscosity higher than the standard. If the amplitude of the oscillation signal at the time of no-adjustment is greater than the reference value by greater than or equal to a predetermined value, the amplitude of the oscillation signal may be damped. This is because, in such a case, the medicinal solution to be atomized is assumed to have a viscosity lower than the standard. Alternatively, if the change in amplitude of the oscillation signal is detected and the amplitude is rapidly increased, the operation of the main body unit may be stopped.

Alternatively, a second atomization unit for spraying a medicinal solution different from the medicinal solution to be sprayed by the atomization unit described above may be provided as a function unit for changing the using method of the nebulizer. The application thus can be made to a treatment method of simultaneously spraying two different types of medicinal solutions.

Alternatively, a unit including a notification section for indicating (e.g., displaying) the elapsed information of the inhaling time and the optimum inhaling timing may be provided as another type of function unit.

Furthermore, in the first to third embodiments, an example of inserting one function unit between the main body unit and the atomization unit has been described. However, since all function units have connection terminals of unified shape, two or more function units may be inserted. For example, the power control unit may be inserted on the main body unit side, and the breath detection unit may be inserted on the atomization unit side. In this case, the oscillation signal after the power control can be output to the atomization unit according to the breathing state.

The mesh type nebulizer has been described by way of example in each embodiment described above, but an ultrasonic nebulizer may be used.

The embodiments disclosed herein are illustrative in all aspects and should not be construed as being restrictive. The scope of the present invention is defined by the Claims rather than by the description made above, and all modifications equivalent in meaning with the Claims and within the scope of the Claims are intended to be encompassed herein.

DESCRIPTION OF SYMBOLS 1 main body unit
2 atomization unit
3 breath detection unit
4 cover unit
5 power control unit
6 extension cord unit
11 power switch
14 power supply circuit
16 oscillation circuit
21 vibrator
31 LED
33 pressure sensor
34 amplifier circuit
35 comparison circuit
36 switch circuit
37 pseudo-resistor
38 power supply circuit
41 mouth piece
42 ventilating portion
50 operating section
51 strong switch
52 normal switch
53 weak switch
54 variable resistor
55 switch terminal
56 operational amplifier
57 amplitude adjusting section
101, 102, 211, 212, 301, 302, 311, 312, 601, 602, 611, 612 connection terminal
103, 303 projection
213, 313 recess
230, 330, 530, 630 attachment tool
240 spray port
241 open/close operating portion
242 liquid retaining portion
244 partition plate,
250 step horn
252 mesh
260 medicinal solution storage section
262 O ring
300, 600 housing
320 fit-in portion
321 first tube portion
322 second tube portion
323 projecting portion
341, 344 substrate
342, 343 sheet metal terminal
350 button type battery
420 tubular portion
421 exhaled air valve
422 attachment member
620 extension cord
1000, 1000A, 1000B nebulizer
2000 nebulizer (of basic specification)

The invention claimed is:

1. A nebulizer for spraying medicinal solution, the nebulizer comprising:
an atomizer, comprising:
a storage section configured to store the medicinal solution, and
an atomizing section configured to spray the medicinal solution by atomizing the medicinal solution in the storage section;
a main body comprising a controller configured to control operation of the atomizing section, the main body being separable from the atomizer and being connectable to the atomizer to perform a basic function of the nebulizer; and
an additional unit for realizing an additional function of the nebulizer, the additional unit being removably attachable between the atomizer and the main body such that (i) when the additional unit is attached between the atomizer and the main body, the nebulizer operates with the additional function, and (ii) when the atomizer and the main body are attached without the additional unit therebetween, the nebulizer operates with the basic function,
wherein the additional unit includes a relay portion configured to electrically connect the controller and the atomizing section.

2. The nebulizer according to claim 1, wherein the additional unit realizes a function of changing a spray state by the atomizing section as the additional function.

3. The nebulizer according to claim 2, wherein the additional unit comprises:
   a detector configured to detect a breathing state of a user of the nebulizer; and
   an atomization controller configured to cause the atomizing section to atomize the medicinal solution only in inhaling of the user according to the detection result by the detector.

4. The nebulizer according to claim 3, wherein:
   the atomizing section includes a vibrator configured to be driven to atomize the medicinal solution;
   the main body further includes an oscillator configured to output an oscillation signal for vibrating the vibrator in response to an instruction from the controller; and
   the atomization controller is configured to receive the oscillation signal output by the oscillator, and to transfer the received oscillation signal to the vibrator only during inhalation of the user.

5. The nebulizer according to claim 2, wherein the additional unit includes an adjuster configured to adjust the spray amount per unit time by the atomizing section.

6. The nebulizer according to claim 5, wherein
   the atomizing section includes a vibrator configured to be driven to atomize the medicinal solution;
   the main body further includes an oscillator configured to output an oscillation signal for vibrating the vibrator in response to an instruction from the controller; and
   the adjuster is configured to adjust the amplitude or the frequency of the oscillation signal output by the oscillator, and to transfer the adjusted oscillation signal to the vibrator.

7. The nebulizer according to claim 5, wherein the additional unit further includes an operating section configured to receive an instruction from the user on the spray amount per unit time.

8. The nebulizer according to claim 1, wherein the additional unit realizes a function of changing a using method of the nebulizer as the additional function.

9. A function unit in combination with an atomizer and a main body of a nebulizer for spraying medicinal solution, (i) the atomizer comprising an atomizing section configured to spray the medicinal solution by atomizing the medicinal solution in a storage section of the atomizer that is configured to store the medicinal solution, and (ii) the main body comprising a controller configured to control operation of the atomizing section, the main body being separable from the atomizer and being connectable to the atomizer to perform a basic function of the nebulizer, the function unit comprising:
   an additional unit for realizing an additional function of the nebulizer, the additional unit being removably attachable between the atomizer and the main body such that (i) when the additional unit is attached between the atomizer and the main body, the nebulizer operates with the additional function, and (ii) when the atomizer and the main body are attached without the additional unit therebetween, the nebulizer operates with the basic function of the nebulizer,
   wherein the additional unit is attached between the atomizer and the main body, and
   wherein the additional unit includes a relay portion configured to electrically connect the controller and the atomizing section.

10. A nebulizer for spraying medicinal solution, the nebulizer comprising:
    an atomizer, comprising:
      a storage section configured to store the medicinal solution, and
      an atomizing section configured to spray the medicinal solution by atomizing the medicinal solution in the storage section;
    a main body comprising a controller configured to control operation of the atomizing section, the main body being separable from the atomizer and being connectable to the atomizer to perform a basic function of the nebulizer; and
    an additional unit for realizing an additional function of the nebulizer, the additional unit being removably attachable between the atomizer and the main body such that (i) when the additional unit is attached between the atomizer and the main body, the nebulizer operates with the additional function, and (ii) when the atomizer and the main body are attached without the additional unit therebetween, the nebulizer operates with the basic function,
    wherein an outer surface of the atomizer includes at least one connection terminal configured (i) to electrically connect the atomizer to the main body by way of at least one connection terminal on an outer surface of the main body and (ii) to electrically connect the atomizer to the additional unit by way of at least one first connection terminal on a first outer surface of the additional unit.

11. The nebulizer according to claim 10, wherein the at least one connection terminal on the outer surface of the main body is configured (i) to electrically connect the main body to the atomizer by way of the at least one connection terminal on the outer surface of the atomizer and (ii) to electrically connect the main body to the additional unit by way of at least one second connection terminal on a second outer surface of the additional unit.

\* \* \* \* \*